United States Patent [19]

Beckett et al.

[11] Patent Number: 5,763,621

[45] Date of Patent: Jun. 9, 1998

[54] METALLOPROTEINASE INHIBITORS

[75] Inventors: Raymond Paul Beckett; Andrew Miller; Mark Whittaker, all of Oxford, United Kingdom

[73] Assignee: British Biotech Pharmaceuticals Limited, Cowley, England

[21] Appl. No.: 776,693

[22] PCT Filed: Aug. 18, 1995

[86] PCT No.: PCT/GB95/01971

§ 371 Date: Feb. 20, 1997

§ 102(e) Date: Feb. 20, 1997

[87] PCT Pub. No.: WO96/06074

PCT Pub. Date: Feb. 29, 1996

[30] Foreign Application Priority Data

Aug. 20, 1994 [GB] United Kingdom ............ 9416897

[51] Int. Cl.$^6$ ........................................... C07D 333/34

[52] U.S. Cl. ................ 549/65; 562/621; 562/623; 514/575; 514/562; 514/564; 514/445; 514/416; 549/62; 548/470; 560/426; 560/450; 560/506

[58] Field of Search ............... 549/62, 65; 562/621, 562/623; 514/575, 562, 564, 445, 416; 548/470; 560/426, 506, 450

*Primary Examiner*—Brian M. Burn
*Attorney, Agent, or Firm*—Banner & Witcoff

[57] ABSTRACT

A compound of formula (I):

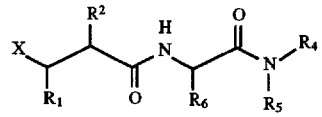

wherein $R_4$ is an optionally substituted $C_3$–$C_8$ cycloalkenyl group. The compounds are inhibitors of matrix metalloproteinases.

12 Claims, No Drawings

METALLOPROTEINASE INHIBITORS

This application is a 35 USC 371 of PCT/GB95/01971, filed Aug. 10, 1995.

The present invention relates to therapeutically active hydroxamic acid and carboxylic acid derivatives, to processes for their preparation, to pharmaceutical compositions containing them, and to the use of such compounds in medicine. In particular, the compounds are inhibitors of metalloproteinases involved in tissue degradation, and in addition are inhibitors of the release of tumour necrosis factor from cells.

BACKGROUND OF THE INVENTION

Compounds which have the property of inhibiting the action of metalloproteinases involved in connective tissue breakdown such as collagenase, stromelysin and gelatinase (known as "matrix metalloproteinases", and herein referred to as MMPs) are thought to be potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and tumour metastasis, invasion and growth. MMP inhibitors are also of potential value in the treatment of neuroinflammatory disorders, including those involving myelin degradation, for example multiple sclerosis, as well as in the management of angiogenesis dependent diseases, which include arthritic conditions and solid tumour growth as well as psoriasis, proliferative retinopathies, neovascular glaucoma, ocular tumours, angiofibromas and hemangiomas. However, the relative contributions of individual MMPs in any of the above disease states is not yet fully understood.

Metalloproteinases are characterised by the presence in the structure of a zinc(II) ionic site. It is now known that there exists a range of metalloproteinase enzymes that includes fibroblast collagenase (Type 1), PMN-collagenase, 72 kDa-gelatinase, 92 kDa-gelatinase, stromelysin, stromelysin-2 and PUMP-1 (J. F. Woessner, FASEB J, 1991, 5, 2145–2154). Many known MMP inhibitors are peptide derivatives, based on naturally occuring amino acids, and are analogues of the cleavage site in the collagen molecule. A recent paper by Chapman et al. (J. Med. Chem. 1993, 36, 4293–4301) reports some general structure/activity findings in a series of N-carboxyalkyl peptides. Other known MMP inhibitors are less peptidic in structure, and may more properly be viewed as pseudopeptides or peptide mimetics. Such compounds usually have a functional group capable of binding to the zinc (II) site in the MMP, and known classes include those in which the zinc binding group is a hydroxamic acid, carboxylic acid, sulphydryl, and oxygenated phosphorus (eg phosphinic acid and phosphonamidate including aminophosphonic acid) groups.

Two known classes of pseudopeptide or peptide mimetic MMP inhibitors have a hydroxamic acid group and a carboxylic group respectively as their zinc binding groups. With a few exceptions, such known MMPs may be represented by the structural formula (I)

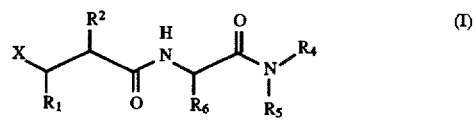

(I)

in which X is the zinc binding hydroxamic acid (—CONHOH) or carboxylic acid (—COOH) group and the groups $R_1$ to $R_5$ are variable in accordance with the specific prior art disclosures of such compounds. Examples of patent publications disclosing such structures are given below.

In such compounds, it is generally understood in the art that variation of the zinc binding group and the substituents $R_1$, $R_2$ and $R_3$ can have an appreciable effect on the relative inhibition of the metalloproteinase enzymes. The group X is thought to interact with metalloproteinase enzymes by binding to a zinc(II) ion in the active site. Generally the hydroxamic acid group is preferred over the carboxylic acid group in terms of inhibitory activity against the various metalloproteinase enzymes. However, the carboxylic acid group in combination with other substituents can provide selective inhibition of gelatinase (EP-489,577-A). The $R_1$, $R_2$ and $R_3$ groups are believed to occupy respectively the P1, P1' and P2' amino acid side chain binding sites for the natural enzyme substrate. There is evidence that a larger $R_1$ substituent can enhance activity against stromelysin, and that a $(C_1-C_6)$alkyl group (such as iso-butyl) at $R_2$ may be preferred for activity against collagenase whilst a phenylalkyl group (such as phenylpropyl) at $R_2$ may provide selectivity for gelatinase over the other metalloproteinases.

Tumour necrosis factor (herein referred to as "TNF") is a cytokine which is produced initially as a cell-associated 28 kD precursor. It is released as an active, 17 kD form, which can mediate a large number of deleterious effects in vivo. When administered to animals or humans it causes inflammation, fever, cardiovascular effects, haemorrhage, coagulation and acute phase responses, similar to those seen during acute infections and shock states. Chronic administration can also cause cachexia and anorexia. Accumulation of excessive TNF can be lethal.

There is considerable evidence from animal model studies that blocking the effects of TNF with specific antibodies can be beneficial in acute infections, shock states, graft versus host reactions and autoimmune disease. TNF is also an autocrine growth factor for some myelomas and lymphomas and can act to inhibit normal haematopoiesis in patients with these tumours.

Compounds which inhibit the production or action of TNF are therefore thought to be potentially useful for the treatment or prophylaxis of many inflammatory, infectious, immunological or malignant diseases. These include, but are not restricted to, septic shock, haemodynamic shock and sepsis syndrome, post ischaemic reperfusion injury, malaria, Crohn's disease, mycobacterial infection, meningitis, psoriasis, congestive heart failure, fibrotic disease, cachexia, graft rejection, cancer, autoimmune disease, rheumatoid arthritis, multiple sclerosis, radiation damage, toxicity following administration of immunosuppressive monoclonal antibodies such as OKT3 or CAMPATH-1 and hyperoxic alveolar injury.

Since excessive TNF production has been noted in several diseases or conditions also characterised by MMP-mediated tissue degradation, compounds which inhibit both MMPs and TNF production may have particular advantages in the treatment or prophylaxis of diseases or conditions in which both mechanisms are involved.

WO 94/10990 discloses that hydroxamic acid based MMP inhibitors in general may be active in inhibiting TNF production. The hydroxamic acid based MMP inhibitors disclosed in WO 93/20047, WO 94/02446 and WO 94/02447 are also stated to be active in inhibiting TNF production.

As mentioned above MMP inhibitors have been proposed with hydroxamic acid or carboxylic acid zinc binding groups. The following patent publications disclose hydroxamic acid- and/or carboxylic acid-based MMP inhibitors:

| | |
|---|---|
| US 4599361 | (Searle) |
| EP-A-2321081 | (ICI) |
| EP-A-0236872 | (Roche) |
| EP-A-0274453 | (Bellon) |
| WO 90/05716 | (British Bio-technology) |
| WO 90/05719 | (British Bio-technology) |
| WO 91/02716 | (British Bio-technology) |
| WO 92/09563 | (Glycomed) |
| US 5183900 | (Glycomed) |
| US 5270326 | (Glycomed) |
| WO 92/17460 | (Smith Kline Beecham) |
| EP-A-0489577 | (Celltech) |
| EP-A-0489579 | (Celltech) |
| EP-A-0497192 | (Roche) |
| US 5256657 | (Sterling Winthrop) |
| WO 92/13831 | (British Bio-technology) |
| WO 92/22523 | (Research Corporation Technologies) |
| WO 93/09090 | (Yamanouchi) |
| WO 93/09097 | (Sankyo) |
| WO 93/20047 | (British Bio-technology) |
| WO 93/24449 | (Celltech) |
| WO 93/24475 | (Celltech) |
| EP-A-0574758 | (Roche) |
| EP-A-0575844 | (Roche) |
| WO 94/02446 | (British Bio-technology) |
| WO 94/02447 | (British Bio-technology) |

BRIEF DESCRIPTION OF THE INVENTION

This invention is based on the finding that in compounds of formula (I) above wherein X is a hydroxamic acid or carboxylic acid group, a $C_3-C_8$ cycloalkyl $R_4$ substituent has in general the unexpected and desirable effect of increasing activity against stromelysin relative to compounds of otherwise similar structure but with acyclic lower alkyl $R_4$ substituents. This finding leads to compounds that are broad spectrum inhibitors of the known metalloproteinases. The class also includes compounds which are orally bioavailable.

In general, metalloproteinase inhibitors known in the art to possess good activity against stromelysin are compounds such as BB-94 (WO 90/05719 Example 2) that possess relatively large substituents at $R_1$. However, BB-94 and compounds with large substituents at $R_1$ tend to be less bioavailable when dosed orally than compounds with smaller or no $R_1$ substituent. A particular advantage of the compounds of the present invention is that the combination of a cycloalkyl $R_4$ substituent with no $R_1$, substituent or a small $R_1$ substituent can provide oral activity together with broad spectrum activity against the metalloproteinase enzymes, including good potency against stromelysin.

In the field of natural peptide analogues the publication by Chapman et al referred to above discloses that aryl groups in the corresponding position to the $R_4$ position of compounds of this invention appear to be preferred for stromelysin activity. The same paper (Supplementary Material) provides data for a natural peptide analogue with a cyclohexyl group in the corresponding position to the $R_4$ position of compounds of this invention, but its activity against stromelysin was lower than the aryl analogues. WO 93/14112 (Merck) discloses compounds with certain aryl groups in the equivalent position. However, compounds of formula (I) above wherein $R_4$ is $C_3-C_8$ cycloalkyl are believed to be novel, and in particular the art does not appear to have recognised the role of a $C_3-C_8$ cycloalkyl $R_4$ substituent in increasing the activity of hydroxamic acid and carboxylic acid based pseudopeptide or peptide mimetic MMP inhibitors against stromelysin.

DETAILED DESCRIPTION OF THE INVENTION

The present invention provides compounds of general formula (I)

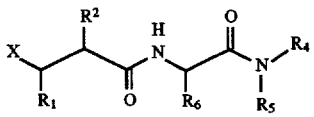

wherein

X is a —$CO_2H$ or —$CONHOH$ group;

$R_1$ is hydrogen; ($C_1-C_6$)alkyl; ($C_2-C_6$)alkenyl; phenyl; substituted phenyl; phenyl ($C_1-C_6$)alkyl); substituted phenyl ($C_1-C_6$)alkyl; heterocyclyl; substituted heterocyclyl; heterocyclyl($C_1-C_6$)alkyl; substituted heterocyclyl($C_1-C_6$) alkyl; a group $BSO_nA$— wherein n is 0, 1 or 2 and B is hydrogen or a ($C_1-C_6$)alkyl, phenyl, substituted phenyl, heterocyclyl, ($C_1-C_6$)acyl, phenacyl or substituted phenacyl group, and A represents ($C_1-C_6$)alkyl; amino; protected amino; acylamino; OH; SH; ($C_1-C_6$)alkoxy; ($C_1-C_6$) alkylamino; di-($C_1-C_6$)alkylamino; ($C_1-C_6$)alkylthio; aryl ($C_1-C_6$)alkyl;amino ($C_1-C_6$)alkyl; hydroxy($C_1-C_6$)alkyl, mercapto($C_1-C_6$)alkyl or carboxy($C_1-C_6$)alkyl wherein the amino-, hydroxy-, mercapto- or carboxyl-group are optionally protected or the carboxyl- group amidated; lower alkyl substituted by carbamoyl, mono(lower alkyl)carbamoyl, di(lower alkyl)carbamoyl, di(lower alkyl)amino, or carboxy-lower alkanoylamino;

$R_2$ is a ($C_1-C_6$)alkyl, ($C_2-C_6$)alkenyl, ($C_2-C_6$)alkynyl, phenyl($C_1-C_6$)alkyl heteroaryl($C_1-C_6$)alkyl, cycloalkyl ($C_1-C_6$)alkyl or cycloalkenyl($C_1-C_6$) alkyl group, any one of which may be optionally substituted by one or more substituents selected from ($C_1-C_6$)alkyl, —O($C_1-C_6$)alkyl, —S($C_1-C_6$)alkyl, —O—phenyl, —O($C_1-C_6$)alkylphenyl, halo and cyano (—CN);

$R_3$ is the characterising group of a natural or non-natural α amino acid in which any functional groups may be protected, PROVIDED that $R_3$ is not a fused or conjugated unsubstituted or substituted bicycloarylmethylene group;

$R_4$ is an optionally substituted $C_3-C_8$ cycloalkyl group or optionally substituted $C_4-C_8$ cycloalkenyl group;

$R_5$ is hydrogen or a ($C_1-C_6$)alkyl group; or a salt, hydrate or solvate thereof.

As used herein the term "($C_1-C_6$)alkyl" or "lower alkyl" means a straight or branched chain alkyl moiety having from 1 to 6 carbon atoms, including for example, methyl, ethyl, n-propyl, isopropyl, n-butyl, isobutyl, sec-butyl, t-butyl, pentyl and hexyl.

The term "($C_2-C_6$)alkenyl" means a straight or branched chain alkenyl moiety having from 2 to 6 carbon atoms and having in addition one double bond of either E or Z stereochemistry where applicable. This term would include, for example, vinyl, 1-propenyl, 1- and 2-butenyl and 2-methyl-2-propenyl.

The term "cycloalkyl" means a saturated alicyclic moiety having from 3–8 carbon atoms and includes, for example, cyclohexyl, cyclooctyl, cycloheptyl, cyclopentyl, cyclobutyl and cyclopropyl.

The term "cycloalkenyl" means an unsaturated alicyclic moiety having from 3–8 carbon atoms and includes, for example, cyclohexenyl, cyclooctenyl, cycloheptenyl, cyclopentenyl, cyclobutenyl and cyclopropenyl. In the case of cycloalkenyl rings of from 5–8 carbon atoms, the ring may contain more than one double bond.

The unqualified term "heterocyclyl" or "heterocyclic" means (i) a 5–7 membered heterocyclic ring containing one or more heteroatoms selected from S, N and O, and optionally fused to a benzene ring, including for example, pyrrolyl, furyl, thienyl, imidazolyl, oxazolyl, thiazolyl, thiadiazolyl, pyrazolyl, pyridinyl, pyrrolidinyl, pyrimidinyl, morpholinyl, piperazinyl, indolyl, benzimidazolyl, maleimido, succinimido, phthalimido, 1,2-dimethyl-3,5-dioxo-1,2,4-triazolidin-4-yl, 3-methyl-2,5-dioxo-1-imidazolidinyl and 3,4,4-trimethyl-2,5-dioxo-1-imidazolidinyl, or (ii) a naphthalimido (ie 1,3-dihydro-1,3-dioxo-2H-benz[f]isoindol-2-yl), 1,3-dihydro-1-oxo-2H-benz[f]isoindol-2-yl, 1,3-dihydro-1,3-dioxo-2H-pyrrolo[3,4-b]quinolin-2-yl, or 2,3-dihydro-1,3-dioxo-1H-benz[d,e]isoquinolin-2-yl group.

The term "5- or 6-membered heterocyclic ring" means such rings having 5 or 6 atoms in the ring, wherein the heteroatom(s) may be one or more nitrogen, oxygen or sulphur atoms, and includes heterocycles containing nitrogen, oxygen, or sulphur alone or containing two nitrogen atoms, a nitrogen and an oxygen atom, a nitrogen and a sulphur atom, two nitrogen atoms and an oxygen atom, two nitrogen atoms and a sulphur.

The "heteroaryl" means a 5-7 membered substituted or unsubstituted aromatic heterocycle containing one or more heteroatoms. Illustrative of such rings are thienyl, furyl, pyrrolyl, imidazolyl, thiazolyl, pyrazolyl, isoxazolyl, isothiazolyl, trizolyl, thiadiazolyl, oxadiazolyl, pyridinyl, pyridazinyl, pyrimidinyl, pyrazinyl and triazinyl.

Unless otherwise specified in the context in which it occurs, the term "substituted" as applied to any moiety herein means substituted with a phenyl group or up to four substituents, each of which independently may be ($C_1$-$C_6$) alkoxy, hydroxy, mercapto, ($C_1$-$C_6$)alkylthio, amino, halo (including fluoro, chloro, bromo and iodo), trifluoromethyl, nitro, —COOH, —CONH$_2$, —CONHR$^A$ or —CONR$^A$R$^A$ wherein R$^A$ is a ($C_1$-$C_6$)alkyl group or the residue of a natural alpha-amino acid.

The term "side chain of a natural or non-natural alpha-amino acid" means the group R in a natural or non-natural amino acid of formula NH$_2$—CH(R)—COOH.

Examples of side chains of natural alpha amino acid include those of glycine, alanine, valine, leucine, isoleucine, phenylalanine, tyrosine, tryptophan, serine, threonine, cysteine, cystine, methionine, asparagine, glutamine, lysine, histidine, arginine, glutamic acid, 5-hydroxylysine, 4-hydroxyproline, proline, alpha amino adipic acid, alpha amino-n-butyric acid, 3,4-dihydroxyphenylalanine, homoserine, alpha methylserine, ornithine, pipecolic acid, thyroxine and aspartic acid.

Natural alpha-amino acids which contain functional substituents, for example amino, carboxyl, hydroxy, mercapto, guanidyl, imidazolyl, or indolyl groups in their characteristic side chains include arginine, lysine, glutamic acid, aspartic acid, tryptophan, histidine, serine, threonine, tyrosine, and cysteine. When R$_3$ in the compounds of the invention is one of those side chains, the functional substituent may optionally be protected.

The term "protected" when used in relation to a functional substituent in a side chain of a natural alpha-amino acid means a derivative of such a substituent which is substantially non-functional. In this context, protected amino groups include amido and acylamino, protected hydroxy or mercapto groups include ethers and thioethers, protected carboxyl groups include esters, and imidazolyl, indolyl or guanidyl groups may be protected as t-butoxycarbonyl derivatives. These are only examples of the many protecting derivatives known in the art, and others will be known to the skilled man.

Examples of side chains of non-natural alpha amino acids include those referred to below in the discussion of suitable R$_3$ groups for use in compounds of the present invention.

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

There are several chiral centres in the compounds according to the invention because of the presence of asymmetric carbon atoms. The presence of several asymmetric carbon atoms gives rise to a number of diastereomers with R or S stereochemistry at each chiral centre. General formula (I), and (unless specified otherwise) all other formulae in this specification are to be understood to include all such stereoisomers and mixtures (for example racemic mixtures) thereof.

In the compounds of the invention, the preferred stereochemistry is in general as follows:

C atom carrying the R$_1$ and X groups—S,

C atom carrying the R$_2$ group—R,

C atom carrying the R$_3$ group—S, but mixtures in which the above configurations predominate are also contemplated.

As previously stated, the compounds of the invention are principally distinguished from the compounds disclosed in the prior art patent publications listed above by the identity of the group R$_4$. Accordingly, the groups R$_1$, R$_2$, R$_3$, and R$_5$ may be any of the groups which have been disclosed in the corresponding positions of compounds disclosed in any of those prior art patent publications listed above. Without limiting the generality of the foregoing, the following classes of substituent R$_3$ have been disclosed in the corresponding position of prior art compounds, and are therefore suitable R$_3$ groups for use in compounds of the present invention:

($C_1$-$C_6$)alkyl, benzyl, hydroxybenzyl, benzyloxybenzyl, ($C_1$-$C_6$)alkoxybenzyl, or benzyloxy($C_1$-$C_6$)alkyl group; and the characterising group of a natural α amino acid, in which any functional group may be protected, any amino group may be acylated and any carboxyl group present may be amidated; and a group -[Alk]$_n$R$_6$ where Alk is a ($C_1$-$C_6$)alkyl or ($C_2$-$C_6$) alkenyl group optionally interrupted by one or more —O—, or —S— atoms or —N(R$_7$)-groups [where R$_7$ is a hydrogen atom or a ($C_1$-$C_6$)alkyl group], n is 0 or 1, and R$_6$ is an optionally substituted cycloalkyl or cycloalkenyl group; and a benzyl group substituted in the phenyl ring by a group of formula OCH$_2$COR$_8$ where R$_8$ is hydroxyl, amino, ($C_1$-$C_6$)alkoxy, phenyl($C_1$-$C_6$)alkoxy, ($C_1$-$C_6$) alkylamino, di(($C_1$-$C_6$)alkyl)amino, phenyl($C_1$-$C_6$) alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; and a heterocyclic(($C_1$-$C_6$)alkyl group, either being unsubstituted or mono- or di-substituted in the heterocyclic ring with halo, nitro, carboxy, ($C_1$-$C_6$)alkoxy, cyano, ($C_1$-$C_6$)alkanoyl, trifluoromethyl ($C_1$-$C_6$)alkyl, hydroxy, formyl, amino, ($C_1$-$C_6$)alkylamino, di-($C_1$-$C_6$)alkylamino, mercapto, ($C_1$-$C_6$)alkylthio, hydroxy($C_1$-$C_6$)alkyl, mercapto($C_1$-$C_6$)alkyl or ($C_1$-$C_6$)alkylphenylmethyl;

R$_3$ may also be a group —CR$_a$R$_b$R$_c$ in which:

each of $R_a$, $R_b$ and $R_c$ is independently hydrogen, $(C_1-C_6)$ alkyl, $(C_2-C_6)$alkenyl, $(C_2-C_6)$alkynyl, phenyl$(C_1-C_6)$ alkyl, $(C_3-C_8)$cycloalkyl, the foregoing being subject to the proviso that $R_a$, $R_b$ and $R_c$ are not all hydrogen; or $R_c$ is hydrogen, $(C_1-C_6)$alkyl, $(C_2-C_6)$alkenyl, $(C_2-C_6)$ alkynyl, phenyl$(C_1-C_6)$alkyl, or $(C_3-C_8)$cycloalkyl, and $R_a$ and $R_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring (for example adamantyl); or $R_a$ and $R_b$ are each independently $(C_1-C_6)$alkyl, $(C_2-C_6)$ alkenyl, $(C_2-C_6)$ alkynyl, phenyl$(C_1-C_6)$alkyl, or a group as defined for $R_c$ below other than hydrogen, or $R_a$ and $R_b$ together with the carbon atom to which they are attached form a 3 to 8 membered cycloalkyl or a 3- to 8-membered heterocyclic ring, and $R_c$ is hydrogen, —OH, —SH, halogen, —CN, —CO$_2$H, $(C_1-C_4)$perfluoroalkyl, —CH$_2$OH, —CO$_2$(C$_1$-C$_6$)alkyl, —O(C$_1$-C$_6$)alkyl, —O(C$_2$-C$_6$)alkenyl, —S(C$_1$-C$_6$)alkyl, —SO(C$_1$-C$_6$) alkyl, —SO$_2$(C$_1$-C$_6$)alkyl, —S(C$_2$-C$_6$)alkenyl, —SO(C$_2$-C$_6$) alkenyl, —SO$_2$(C$_2$-C$_6$)alkenyl or a group —Q—W wherein Q represents a bond or —O—, —S—, —SO— or —SO$_2$— and W represents a phenyl, phenylalkyl, $(C_3-C_8)$cycloalkyl, $(C_3-C_8)$cycloalkylalkyl, $(C_4-C_8)$cycloalkenyl, $(C_4-C_8)$ cycloalkenylalkyl, heteroaryl or heteroarylalkyl group, which group W may optionally be substituted by one or more substituents independently selected from, hydroxyl, halogen, —CN, —CO$_2$H, —CO$_2$(C$_1$-C$_6$)alkyl, —CONH$_2$, —CONH(C$_1$-C$_6$)alkyl, —CONH(C$_1$-C$_6$alkyl)$_2$, —CHO, —CH$_2$OH, (C$_1$-C$_4$)perfluoroalkyl, —O(C$_1$-C$_6$)alkyl, —S(C$_1$-C$_6$)alkyl, —SO(C$_1$-C$_6$)alkyl, —SO$_2$(C$_1$-C$_6$)alkyl, —NO$_2$, —NH$_2$, —NH(C$_1$-C$_6$)alkyl, —N((C$_1$-C$_6$)alkyl)$_2$, —NHCO(C$_1$-C$_6$)alkyl, (C$_1$-C$_6$)alkyl, (C$_2$-C$_6$)alkenyl, (C$_2$-C$_6$)alkynyl, (C$_3$-C$_3$)cycloalkyl, (C$_4$-C$_8$)cycloalkenyl, phenyl or benzyl.

More specifically with respect to the groups $R_1$, $R_2$, $R_3$, $R_4$ and $R_5$ in compounds of the invention:

Examples of particular $R_1$ groups include hydrogen, methyl, ethyl, hydroxyl, methoxy, allyl, thienylsulphanylmethyl, thienylsulphinylmethyl, thienylsulphonylmethyl and phthalimidomethyl. Presently preferred are compounds in which $R_1$ is hydrogen, hydroxyl, allyl or phthalimidomethyl.

Examples of particular $R_2$ groups include iso-butyl, n-pentyl, n-hexyl, n-heptyl, n-octyl, n-nonyl, n-decyl, cyclohexylpropyl, phenylpropyl, 3-phenyl-prop-2-enyl, 4-chlorophenylpropyl, 4-methylphenylpropyl, 4-methoxyphenylpropyl, pyrid-4-ylpropyl, phenylbutyl, benzyloxybutyl, phenoxybutyl, propyloxymethyl and propylsulphanyl. Presently preferred are compounds in which $R_2$ is isobutyl, n-heptyl, or phenylpropyl.

Examples of particular $R_3$ groups include benzyl, iso-butyl or t-butyl, 1 -fluoro-1-methylethyl, 1-hydroxy-1-methylethyl, 1-methoxy-1-methylethyl, 1-benzylthio-1-methylethyl, and 1-mercapto-1-methylethyl. Presently preferred are compounds in which $R_3$ is t-butyl or 1-mercapto-1-methylethyl.

Examples of particular $R_4$ groups are cyclopropyl, 2-phenylcyclopropyl, cyclobutyl, cyclopentyl, cyclohexyl, cycloheptyl and cyclooctyl.

$R_5$ is preferably hydrogen.

Specific compounds of the invention include:

$N^4$-(1S-Cyclobutylcarbamoyl-2,2-dimethyl-propyl)-2S, $N^1$-dihydroxy-3R-isobutyl-succinamide $N^4$-(1S-Cyclopropylcarbamoyl-2,2-dimethyl-propyl)-2S, $N^1$-dihydroxy-3R-isobutyl-succinamide $N^4$-(1S-Cyclopentylcarbamoyl-2,2-dimethyl-propyl)-2S, $N^1$-dihydroxy-3R-isobutyl-succinamide $N^4$-(1S-Cyclohexylcarbamoyl-2,2-dimethyl-propyl)-2S, $N^1$-dihydroxy-3R-isobutyl-succinamide $N^4$-(1S-Cycloheptylcarbamoyl-2,2-dimethyl-propyl)-2S, $N^1$-dihydroxy-3R-isobutyl-succinamide $N^4$-(1S-Cyclopropylcarbamoyl-2-mercapto-2-methylpropyl)-2S,$N^1$-dihydroxy-3R-isobutyl-succinamide $N^4$-(1S-Cyclopropylcarbamoyl-2,2-dimethyl-propyl)-2S, $N^1$-dihydroxy-3-(3-phenyl-propenyl) -succinamide $N^4$-(1S-Cyclopropylcarbamoyl-2,2-dimethyl-propyl)-2S, $N^1$-dihydroxy-3R-(3-phenyl-propyl) -succinamide $N^4$-[2,2-Di methyl-1S-(2-phenyl-cyclopropylcarbamoyl)-propyl]-2S, $N^1$-dihydroxy-3R-isobutyl -succinamide 2A-Allyl-$N^4$-(1-cyclopropylcarbamoyl-2,2-dimethylpropyl)-$N^1$-hydroxy-3R-isobutyl-succinamide 2-Allyl-$N^4$-(1S-cyclopropylcarbamoyl-2-mercapto-2-methyl-propyl)-$N^1$-hydroxy-3R-isobutyl -succinamide $N^4$-(1S-Cyclopropylcarbamoyl-2,2-dimethyl-propyl)-$N^1$-hydroxy-3R-isobutyl-2S-(thiophen-2-ylsulfanylmethyl)-succinamide $N^4$-(1S-Cyclopropylcarbamoyl-2,2-dimethyl-propyl)-$N^1$-hydroxy-2S-(4-hydroxy-phenylsulfanylmethyl)-3R-isobutyl-succinamide $N^4$-(1S-Cyclopropylcarbamoyl-2,2-dimethyl-propyl)-2S-(1,3-dioxo-1,3-dihydroisoindol-2-ylmethyl)-$N^1$-hydroxy-3R-isobutyl-succinamide and salts, solvates or hydrates thereof.

Compounds according to the present invention in which X is a hydroxamic acid group —CONHOH may be prepared from corresponding compounds of the invention in which X is a carboxylic acid group —COOH or from the corresponding protected hydroxamic acid derivatives. That process, which forms another aspect of the invention, comprises:

(a) causing an acid of general formula (II)

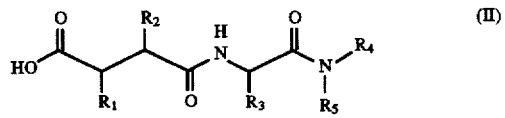

or an activated derivative thereof to react with hydroxylamine, O-protected hydroxylamine, or an N,O-diprotected hydroxylamine, or a salt thereof, $R_1$, $R_2$, $R_3$, $R_4$, and $R_5$ being as defined in general formula (I) except that any substituents in $R_1$, $R_2$, $R_3$, $R_4$, and $R_5$ which are potentially reactive with hydroxylamine, O-protected hydroxylamine, the N,O-diprotected hydroxylamine or their salts may themselves be protected from such reaction, then removing any protecting groups from the resultant hydroxamic acid moiety and from any protected substituents in $R_1$, $R_2$, $R_3$, $R_4$, and $R_5$; or (b) deprotecting a diprotected hydroxamic acid derivative of formula (IIb)

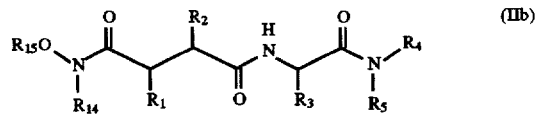

in which $R_1$, $R_2$, $R_3$, $R_4$, and $R_5$ are as defined in general formula (I), $R_{14}$ is an amino protecting group and $R_{15}$ is a hydroxyl protecting group.

For method (a) conversion of (II) to an activated derivative such as the pentafluorophenyl, hydroxysuccinyl, or hydroxybenzotriazolyl ester may be effected by reaction with the appropriate alcohol in the presence of a dehydrating agent such as dicyclohexyl dicarbodiimide (DCC), N,N-dimethylaminopropyl-N'-ethyl carbodiimide (EDC), or 2-ethoxy-1-ethoxycarbonyl-1,2-dihydroquinoline (EEDQ).

Protecting groups as referred to above are well known per se, for example from the techniques of peptide chemistry. Amino groups are often protectable by benzyloxycarbonyl, t-butoxycarbonyl or acetyl groups, or in the form of a phthalimido group. Hydroxy groups are often protectable as readily cleavable ethers such as the t-butyl or benzyl ether, or as readily cleavable esters such as the acetate. Carboxy groups are often protectable as readily cleavable esters, such as the t-butyl or benzyl ester.

Examples of O-protected hydroxylamines for use in method (a) above include O-benzylhydroxylamine, O-4-methoxybenzylhydroxylamine, O-trimethylsilylhydroxylamine, and O-tert-butoxycarbonylhydroxylamine.

Examples of O,N-diprotected hydroxylamines for use in method (a) above include N,O-bis(benzyl)hydroxylamine, N,O-bis(4-methoxybenzyl)hydroxylamine, N-tert-butoxycarbonyl-O-tert-butyldimethylsilylhydroxylamine, N-tert-butoxycarbonyl-O-tetrahydropyranylhydroxylamine, and N,O-bis(tert-butoxycarbonyl)hydroxylamine.

For method (b) suitable protecting groups $R_{14}$ and $R_{15}$ are benzyl and substituted benzyl (eg 4-methoxybenzyl). Such protecting groups may be removed by hydrogenolysis, while the 4-methoxybenzyl group may also be removed by acid hydrolysis.

In method (a) in the special case where $R_1$ in compound (I) is hydroxy, it too may be protected during the coupling of compounds (III) and (IV). In that case a particularly useful technique may be simultaneous protection of the hydroxy group $R_1$ and the adjacent carboxyl group as a dioxalone of formula (IIa):

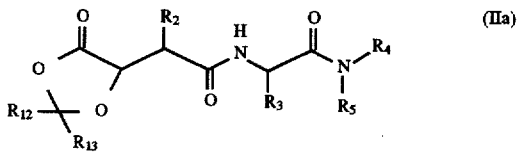

wherein the groups $R_{12}$ and $R_{13}$ are derived from a dioxalone forming reagent, and may be, for example, hydrogen, alkyl, phenyl or substituted phenyl. The dioxalone ring being is opened on reaction with hydroxylamine to give the required hydroxamic acid derivative of formula (I).

Compounds according to the present invention in which X is a carboxylic acid group —COOH may be prepared by a process comprising: coupling an acid of formula (III) or an activated derivative thereof with an amine of formula (IV)

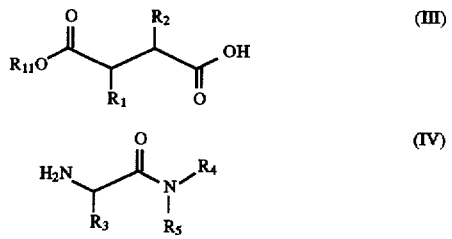

wherein $R_1$, $R_2$, $R_3$, $R_4$, and $R_5$ are as defined in general formula (I) except that any substituents in $R_1$, $R_2$, $R_3$, $R_4$, and $R_5$ which are potentially reactive in the coupling reaction may themselves be protected from such reaction, and $R_{11}$ represents a hydroxy protecting group, and subsequently removing the protecting group $R_{11}$ and any protecting groups from $R_1$, $R_2$, $R_3$, $R_4$, and $R_5$.

Active derivatives of acids (III) include activated esters such as the pentafluorophenyl ester, acid anhydrides and acid halides, eg chlorides. Suitable hydroxy protecting groups may be selected from those known in the art.

In the special case where $R_1$ in compound (III) is hydroxy, it too may be protected during the coupling of compounds (III) and (IV). In that case a particularly useful technique may be simultaneous protection of the two hydroxy groups as a dioxalone of formula (V):

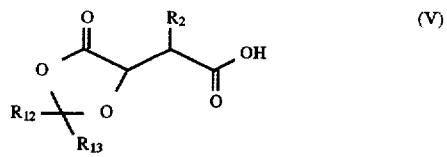

wherein the groups $R_{12}$ and $R_{13}$ are derived from a dioxalone forming reagent, and may be, for example, hydrogen, alkyl, phenyl or substituted phenyl.

As mentioned above, compounds of formula (I) are useful in human or veterinary medicine since they are active as inhibitors of MMPs, and a further advantage lies in their ability to inhibit the release of tumour necrosis factor (TNF) from cells.

Accordingly in another aspect, this invention concerns:

(i) a method of management (by which is meant treatment or prophylaxis) of diseases or conditions mediated by MMPs and/or TNF in mammals, in particular in humans, which method comprises administering to the mammal an effective amount of a compound as defined with respect to formula (I) above, or a pharmaceutically acceptable salt thereof; and (ii) a compound as defined with respect to formula (I) for use in human or veterinary medicine, particularly in the management (by which is meant treatment or prophylaxis) of diseases or conditions mediated by MMPs and/or TNF; and (iii) the use of a compound as defined with respect to formula (I) in the preparation of an agent for the management (by which is meant treatment or prophylaxis) of diseases or conditions mediated by MMPs and/or TNF.

Diseases or conditions mediated by MMPs include those involving tissue breakdown such as bone resorption, inflammatory diseases, dermatological conditions and tumour invasion by secondary metastases, in particular rheumatoid arthritis, osteoarthritis, periodontitis, gingivitis, corneal ulceration and tumour invasion by secondary metastases. Diseases or conditions mediated by TNF include inflammation, fever, cardiovascular effects, haemorrhage, coagulation and acute phase response, cachexia and anorexia, acute infections, shock states, graft versus host reactions and autoimmune disease.

In a further aspect of the invention there is provided a pharmaceutical or veterinary composition comprising a compound of formula (I) together with a pharmaceutically or veterinarily acceptable excipient or carrier. In view of the water-solubility, and oral bioavailability advantages of compounds in accordance with the invention, a further aspect of the invention comprises a pharmaceutical or veterinary composition comprising a compound of formula (I) together with a pharmaceutically or veterinarily acceptable excipient or carrier, characterised in that the composition is adapted for oral administration.

One or more compounds of general formula (I) may be present in the composition together with one or more excipient or carrier.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The dosage unit involved in oral administration may contain from about 1 to 250 mg, preferably from about 25 to 250 mg of a compound of the invention. A suitable daily dose for a mammal may vary widely depending on the condition of the patient. However, a dose of a compound of general formula I of about 0.1 to 300 mg/kg body weight, particularly from about 1 to 100 mg/kg body weight may be appropriate.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite os disodium edeate; preservatives including bactericidal and fungicidal agents such as phenyl mercuric acetate or nitrate, benzalkonium chloride or chlorhexidine, and thickening agents such as hypromellose may also be included.

The dosage for topical administration will of course depend on the size of the area being treated. For the eyes, each dose may typically be in the range from 10 to 100 mg of the drug.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

For use in the treatment of rheumatoid arthritis, the drug can be administered by the oral route or by injection intra-articularly into the affected joint. The daily dosage for a 70 kg mammal may be in the range 10 mgs to 1 gram.

The following Examples illustrate embodiments of the invention:

The amino acids used in the examples were commercially available or were prepared according to literature procedures.

The following abbreviations have been used throughout:

| | |
|---|---|
| EDC | N-Ethyl-N'-(3-dimethylaminopropyl)carbodiimide hydrochloride |
| DIPE | Diisopropyl ether |
| DMF | N,N-Dimethylformamide |
| HOBt | 1-Hydroxybenzotriazole |
| LDA | Lithium diisopropylamide |
| NMM | N-Methylmorpholine |
| THF | Tetrahydrofuran |
| TFA | Trifluoroacetic acid |
| TLC | Thin layer chromatography |

$^1$H and $^{13}$C NMR spectra were recorded using a Bruker AC 250E spectrometer at 250.1 and 62.9 MHz, respectively. Elemental microanalyses were performed by either CHN Analysis Ltd., Alpha House, Countesthorpe Road, South Wigston, Leicester LE8 2PJ, UK, or MEDAC Ltd., Dept. of Chemistry, Brunel University, Uxbridge, Middlesex UB8 3PH, UK.

EXAMPLE 1

$N^4$-(1S-Cyclobutylcarbamoyl-2,2-dimethyl-propyl)-2S, $N^1$-dihydroxy-3R-isobutyl-succinamide

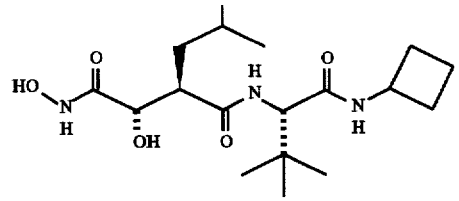

STEP A:
2S-Hydroxy-3R-(2-methyl-allyl)-succinic acid diisopropyl ester

2S-Hydroxy-succinic acid diisopropyl ester (50 g, 230 mmol) was added to a solution of LDA [from N,N-diisopropylamine (80 ml, 570 mmol) and 10M n-butyllithium (48.1 ml, 481 mmol)] in dry THF (500 ml) whilst maintaining the temperature at −70° C. When addition was complete the reaction was warmed to −15° C. and stirred for 8 hours. The reaction mixture was cooled to −70° C. and methallyl iodide (46 g, 252 mmol) was added slowly, ensuring that the temperature did not exceed −65° C. The mixture was warmed to −40° C. and stirred for 18 hours before quenching at −15° C. with citric acid. The organic layer was separated and washed with 10% NaHCO$_3$ solution (500 ml) and brine (300 ml) then dried (MgSO$_4$). The solution was filtered and concentrated in vacua to give a brown oil (64 g) which was purified by column chromatography (silica gel, 1 kg, gradient elution with 20 to 35% diethyl ether in hexane). The desired product was isolated as a colourless oil (30.9 g, 49%) which was found to be a 17:1 mixture of diastereomers by NMR. $^1$H-NMR; δ (CDCl$_3$, major diastereomer), 5.06 (1H, septet, J=6.3 Hz), 4.97 (1H, septet, J=6.3 Hz), 4.78 (2H, d, J=7.1 Hz), 4.16 (1H, m), 3.20 (1H, d, J=6.2 Hz), 3.00 (1H, m), 2.50, 2.35 (2H, ABX, J=7.0, 8.7, 14.4 Hz), 1.72 (3H, s) and 1.24-1.16 (12H, 2 m).

STEP B:
2S-Hydroxy-3R-isobutyl-succinic acid diisopropyl ester

2S-Hydroxy-3R-(2-methyl-allyl)-succinic acid diisopropyl ester (7.14 g, 26.2 mmol) was dissolved in ethanol (80 ml), and stirred overnight with 10% palladium on charcoal catalyst (1.0 g) under an atmosphere of hydrogen. The catalyst was removed by filtration and the filtrate was evaporated to dryness to leave the product as a clear oil (7.03 g, 98%). $^1$H-NMR; δ (CDCl$_3$), 5.06 (1H, septet, J=6.3 Hz), 4.97 (1H, septet, J=6.3 Hz), 4.17 (1H, br s,), 3.24 (1H, br s), 2.83 (1H, m), 1.68 (2H,m), 1.44 (1H, m), 1.24 (6H, d, J=6.2 Hz), 1.18 (6H, d, J=6.2 Hz) and 0.89 (6H, m)

STEP C:

2S-Hydroxy-3R-isobutyl-succinic acid

2S-Hydroxy-3R-isobutyl-succinic acid diisopropyl ester (7.0 g, 25.6 mmol) was dissolved in dioxane (15 ml) and water (15 ml), a solution of KOH (4.29 g) in water (22 ml) was added and the mixture was heated at 90° C. overnight. The solution was allowed to cool and then passed through an ion exchange resin (Dowex 50X4-400, 200 ml) and evaporated to yield the title compound (4.82 g, 99%). $^1$H-NMR; δ (CDCl$_3$), 8.70 (2H, br s), 4.32 (1 H, br s), 3.10 (1H, m), 1.85-1.55 (3H, m) and 0.96 (6H, m).

STEP D:

2R-(2,2-Dimethyl-5-oxo-[1,3]dioxalan-4S-yl)-4-methylpentanoic acid

2S-Hydroxy-3R-isobutyl-succinic acid (5.19 g, 27.3 mmol) was dissolved in 2,2-dimethoxypropane (150 ml) and DMF (40 ml) and stirred overnight at 30° C. in the presence of a catalytic amount of p-toluene sulphonic acid. The solvent was removed to give the title compound contaminated with solvent (6.87 g, crude). $^1$H-NMR; δ (CDCl$_3$), 4.41 (1H, d, J=4.8 Hz), 2.91 (1H, m), 1.69 (3H, m), 1.54 (3H, s), 1.48 (3H, s) and 0.88 (6H, m).

STEP E:

2R-(2,2-Dimethyl-5-oxo-[1,3]dioxalan-4S-yl)-4-methylpentanoic acid pentafluorophenyl ester 2R-(2,2-Dimethyl-5-oxo-[1,3]dioxalan-4S-yl)-4-methylpentanoic acid (558 mg, 2.4 mmol) was taken up in dichloromethane (10 ml) and cooled to 0° C. before adding pentafluorophenol (670 mg, 3.6 mmol) and EDC (560 mg, 2.9 mmol). The reaction was stirred at 0° C. for 2 hours then the solution was washed with 1M sodium carbonate (50 ml) and brine (20 ml). The organic layer was dried (magnesium sulphate), filtered, evaporated to dryness and purified by column chromatography (silica gel, dichloromethane) to give the activated ester (552 mg, 58%). $^1$H-NMR; δ (CDCl$_3$), 4.57 (1H, d, J=6.5 Hz), 3.32 (1H, m), 1.86 (3H, m), 1.67 (3H, s), 158 (3H, s) and 1.03 (6H, m).

STEP F:

N$^α$-Benzyloxycarbonyl-L-tert-leucine-N-cyclobutylamide

N$^{60}$ - Benzyloxycarbonyl-L-tert-leucine(4.90 g, 18.42 mmol) was dissolved in DMF (30 ml) and the solution was cooled to 0° C. and stirred during the addition of HOBt (2.98 g, 22.10 mmol) and EDC (4.23 g, 22.10 mmol). The mixture was allowed to warm to room temperature, stirred for a further 1 hour then cooled back to 0° C. Cyclobutylamine (2.35 ml, 27.63 mmol) was then added dropwise and the mixture was warmed to room temperature then stirred for 48 hours. Solvent was evaporated and the residue dissolved in ethyl acetate and washed with 1N HCl and 1N NA$_2$CO$_3$ before drying over anhydrous MgSO$_4$. The solution was filtered and evaporated to afford the title compound as a white solid (4.65 g, 79%). $^1$H-NMR; δ (CDCl$_3$), 7.38-7.30 (5H, m), 6.04 (1H, d), 5.59 (1H, d), 2.33 (2H, m), 1.92-1.78 (2H, m) 170 (2H, m) and 0.98 (9H, s).

STEP G:

L-tert-Leucine-N-cyclobutylamide

N$^α$-Benzyloxycarbonyl-L-tert-leucine-N-cyclobutylamide (4.65 g, 17.28 mmol) was dissolved in ethanol (100 ml) and 10% palladium on charcoal (460 mg) was added. Hydrogen gas was then bubbled through the mixture for 2 hours. The catalyst was removed by filtration and the solvent evaporated to leave the title compound (2.69 g, including residual ethanol) which was used without further purification $^1$H-NMR; δ (CDCl$_3$), 6.86 (1H, br s), 4.35 (1H, m), 2.99 (1H, s), 2.29 (2H, m), 1.86-1.58 6, m and 0.94 (9H, s).

STEP H:

2R-(2,2-Dimethyl-5-oxo-[1,3]dioxalan-4S-yl)-4-methylpentanoic acid (1S-cyclobutylcarbamoyl-2,2-dimethylpropyl)-amide 2R-(2,2-Dimethyl-5-oxo-[1,3]dioxalan-4S-yl)-4-methylpentanoic acid pentafluorophenyl ester (5.79 g, 14.62 mmol) and L-tert-leucine-N-cyclobutylamide (2.69 g, 14.62 mmol) were dissolved in DMF (30 ml) and the mixture was stirred overnight at room temperature. The solvent was removed to give an oil which dissolved in ethyl acetate and the solution was washed twice with 1M Na$_2$CO$_3$ and then with brine. The organic phase was dried (MgSO$_4$), filtered and evaporated to an oil which was purified by column chromatography (flash silica, ethyl acetate: hexane, 1:2) to provide the title compound as a white foam (3.72 g, 65%). $^1$H-NMR; δ (CDCl$_3$), 6.62 (1H, d, J=8.9 Hz), 6.05 (1H, d, J=7.7 Hz), 4.48 (1H, d, J =6.0 Hz), 4.35 (1H, m), 2.32 (2H, m), 1.88-1.59 (10H, m), 1.53 (3H, s), 0.99 (9H, s) and 0.89 (6H, m).

STEP 1:

N$^4$-(1S-Cyclobutylcarbamoyl-2,2-dimethyl-propyl)-2S, N$^1$-dihydroxy-3R-isobutyl-succinamide To a solution of hydroxylamine hydrochloride (3.27 g, 47.08 mmol) in methanol (50 ml) was added sodium methoxide (2.54 g, 47.08 mmol) and the mixture was stirred at room temperature for 2 hours, after which time the precipitated solid was removed by filtration. The filtrate was cooled in an ice bath prior to the addition of 2R-(2,2-dimethyl-5-oxo-[1,3]dioxalan-4S-yl)-4-methyl-pentanoic acid (1S-cyclobutylcarbamoyl-2,2-dimethyl-propyl)-amide (3.72 g, 9.41 mol) dissolved in DMF (15 ml) and methanol (50 ml). The mixture was stirred at 0° C. for 10 minutes then allowed to warm to room temperature and stirred overnight. The solvent was removed under reduced pressure and the residue was partitioned between diethyl ether (50 ml) and water (50 ml). The mixture was allowed to stand at room temperature overnight, during which time a white solid precipitated. This was collected by filtration and washed with diethyl ether and water before drying under reduced pressure. Yield: 1.79 g (44%). 1H NMR; δ (CD$_3$OD), 8.25 (1H, d, J=7.3 Hz), 4.21 (2H, m), 3.99 (1H, d, J=6.3 Hz), 2.82 (1H, m), 2.21 (2H, m), 191 (2H, m), 1.60 (4H, m), 1.21 (1H, m), 0.95 (9H, s), 0.88 (3H, d, J=6.5 Hz) and 0.85 (3H, d, J=6.4 Hz). $^{13}$C-NMR; δ (CD$_3$OD), 175.5, 171.5, 73.1, 61.8, 45.9, 39.6, 35.5, 31.3, 31.1, 27.2, 27.0, 23.7, 22.4, 16.2, 13.7 and 13.5. ν max (KBr); 2957, 1651, 1520, 1368, 1148, 1064 cm$^{-1}$.

The compounds of Examples 2–9 were prepared by the methods of Example 1, from the appropriate starting materials.

EXAMPLE 2

N⁴-(1S-Cyclopropylcarbamoyl-2,2-dimethyl-propyl)-2S, N¹-dihydroxy-3R-isobutyl-succinamide

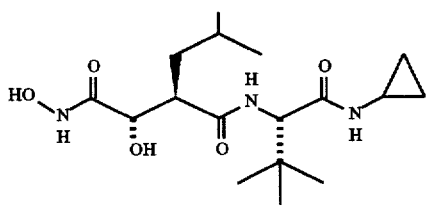

White solid. m.p. 102°–103° C. ¹H NMR; δ (CD₃OD), 4.14 (1H, s), 4.00 (1H, d, J=6.0 Hz), 2.85-2.77 (1H, m), 2.64-2.55 (1H, m), 1.64-1.43 (2H, m), 1.27-1.17 (1H, m), 0.94 (9H, s), 0.90-0.84 (6H, dd, J=6.0, 9.0 Hz), 0.72-0.62 (2H, m) and 0.54-0.41 (2H, m). ¹³C-NMR; δ (CD₃OD), 175.5, 174.2, 171.6, 169.2, 73.0, 61.7, 39.6, 35.5, 27.2, 27.0, 23.6, 23.2, 22.4, 6.5 and 6.4.

EXAMPLE 3

N⁴-(1 S-Cyclopentylcarbamoyl-2,2-dimethyl-propyl)-2S, N¹-dihydroxy-3R-isobutyl--succinamide

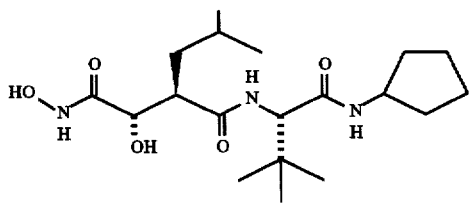

White solid. m.p. 103°–104° C. ¹H NMR; δ (CD₃OD), 7.98 (1H, d, J=7.1 Hz), 4.21 (1H, s), 4.05 (1H, s), 3.99 (1H, d, J=6.3 Hz), 2.82 (1H, m), 1.85 (2H, m), 148 (8H m), 1.21 (1H, m), 0.95 (9H, s), 0.89 (3H, d, J=6.4Hz) and 0.85 (3H, d, J=6.5 Hz). ¹³C-NMR; δ (CD₃OD), 175.4, 172.0, 171.5, 73.1, 61.7, 52.4, 49.5, 39.6, 35.5, 33.5, 33.3, 27.2, 27.0, 24.77, 23.7 and 22.4.

EXAMPLE 4

N⁴-(1 S-Cyclohexylcarbamoyl-2,2-dimethyl-propyl)-2S, N¹-dihydroxy-3R-isobutyl-succinamide

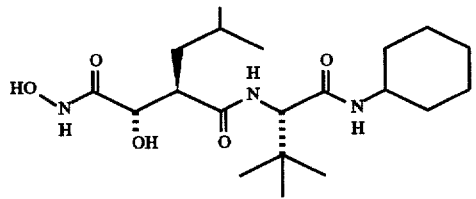

White solid. m.p. 108° C. (decomposed). ¹H NMR; δ (CD₃OD), 4.19 (1H, s), 3.99 (1 H, d, J=6.3Hz), 3.60 (1H, m), 2.81 (1H, m), 1.87-1.07 (13H, br m), 0.96 (9H, s), 0.89 (3H, d, J=6.5 Hz) and 0.85 (3H, d, J=6.5 Hz). ¹³C-NMR; δ (CD₃OD) 175.4, 171.5, 171.4, 73.1, 61.9, 49.8, 49.5, 39.6, 35.5, 33.8, 33.6, 27.2, 27.0, 26.6, 26.1, 23.7 and 22.4. Found: C, 59.19%, H, 9.23% N, 10.01%; C₂₀H₃₇N₃O₅0.4 H₂O requires C, 59.06%, H, 9.37% N, 10.33%

EXAMPLE 5

N⁴-(1S-Cycloheptylcarbamoyl-2,2-dimethyl-propyl)-2S, N¹-dihydroxy-3R-isobutyl-succinamide

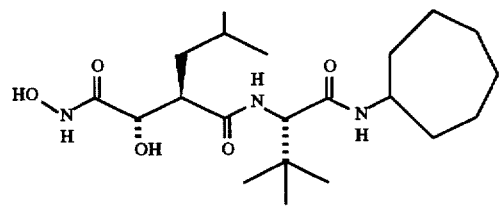

White solid. ¹H-NMR; δ (CD₃OD), 7.86 (1H, d, J=7.6 Hz), 4.12 (1 H, s), 3.91 (1H, d, J=6.3 Hz), 3.73 (1H, br s), 2.74 (1H, m), 1.76 (2H, m), 1.51 (13H, m), 1.53 (1H,m), 0.89 (9H, s) and 0.80 (6H, dd, J=9.1, 6.5 Hz). ¹³C-NMR; δ (CD₃OD), 175.4, 171.5, 171.0, 73.1, 61.9, 51.9, 39.6, 35.9, 35.6, 35.5, 29.3, 29.2, 27.2, 27.0, 25.3, 23.7 and 22.4.

EXAMPLE 6

N⁴-(1 S-Cyclopropylcarbamoyl-2-mercapto-2-methyl-propyl)-2S, N¹-dihydroxy-3R-isobutyl-succinimide

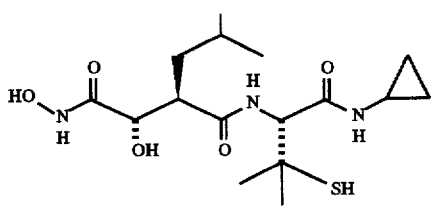

White foam (6:1 mixture of diastereoisomers). ¹H-NMR; δ (CD₃OD), 4.36 (0.15H, s), 4.34 (0.85H, s), 3.92 (0.85H, d, J=6.5 Hz), 3.89 (0.15H, d, J=6.4 Hz), 2.76 (1H, m), 2.55 (1H, m), 1.58-1.11 (9H, 2s and br m), 0.82 (3H, d, J=6.4 Hz), 0.79 (3H,d, J=6.5 Hz), 0.61 (2H, m) and 0.41 (2H, m). ¹³C-NMR; δ (CD₃OD), 175.5, 173.1, 171.5, 73.1, 62.2, 49.5, 46.8, 39.5, 31.2, 29.2, 27.0, 23.7, 23.3, 22.2 and 6.4. IR;ν_max(KBr); 3292, 2959, 2871, 1644, 1530, 1464, 1388, 1300, 1259 and 1204 cm⁻¹. Found: C 50.68, H 7.80, N 10.85%; C₁₆H₂₉N₃O₅S. 0.2 H₂O requires C 50.69, H 7.82, N 11.08%.

EXAMPLE 7

N⁴-(1S-Cyclopropylcarbamoyl-2,2-dimethyl-propyl)-2S, N¹-dihydroxy-3R-(3-phenylpropenyl)-succinamide

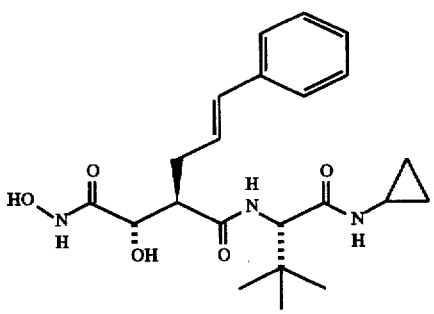

Pale yellow foam. m.p. 109.5°–111.5° C. ¹H-NMR; δ (CD₃OD), 7.12 (5H, m), 6.32 (1H, d, J=15.8 Hz), 6.04 (1H, m), 4.07 (2H, m), 2.85 (1H, m), 2.36 (3H, m), 0.86 (9H, s), 0.48 (2H, m) and 0.26 (2H, m). $^{13}$C-NMR; δ (CD$_3$OD), 174.7, 173.9, 171.7, 138.7, 133.6, 129.5, 128.2, 127.2, 72.5, 61.6, 51.1, 35.6, 33.9, 27.1, 23.1, 6.5 and 6.2. IR;ν$_{max}$(KBr); 3296, 2964, 1642, 1534, 1369, 1259, 1073, 1025 and 967 cm$^{-1}$. Found: C 61.79, H 7.44, N 9.54%; C$_{22}$H$_{31}$N$_3$O$_5$.0.6 H$_2$O requires C 61.69, H 7.58, N 9.81%.

EXAMPLE 8

N$^4$-(1 S-Cyclopropylcarbamoyl-2,2-dimethyl-propyl)-2S, N$^1$-dihydroxy-3R-(3-phenylpropyl)-succinamide

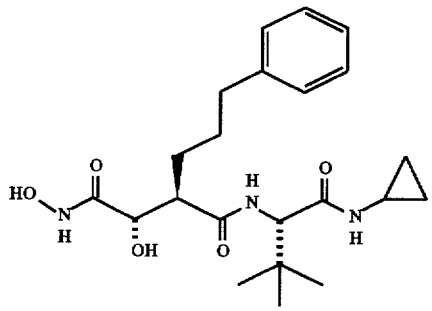

White solid. m.p. 101°–103° C. $^1$H-NMR; δ (CD$_3$OD), 8.10 (1H, s), 7.77 (1H, d, J=8.5 Hz), 7.08 (5H, m), 4.08 (1H, m), 3.95 (1H, m), 2.67 (1H, m), 2.50 (3H, m), 1.65-130 (4H, m), 0.86 (9H, s), 0.57 (2H, m) and 0.34 (2H, m). $^{13}$C-NMR; δ (CD$_3$OD), 175.3, 174.1, 171.5, 143.3, 129.4, 126.8, 72.9, 61.7, 51.1, 36.7, 35.5, 30.4, 30.2, 27.2, 23.2 and 6.4. IR;ν$_{max}$ (KBr); 3288, 3026, 2956, 2868, 2484, 1651, 1538, 1454, 1399, 1369, 1236, 1190, 1077, 1029, 926, 825, 749 and 700 cm$^{-1}$. Found: C 61.58, H 7.91, N 9.80%; C$_{22}$H$_{33}$N$_3$O$_5$.0.5 H$_2$O requires C 61.66, H 8.00, N 9.81%.

EXAMPLE 9

N$^4$-[2,2-Dimethyl-1S-(2-phenyl-cyclopropylcarbamoyl)-propyl]-2S, N$^1$-dihydroxy-3R-isobutyl-sucinamide

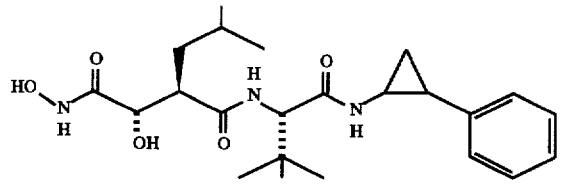

White foam. m.p. 119°–121 ° C. $^1$H-NMR; δ (CD$_3$OD), 7.12 (5H, m), 4.07 (2H, m), 3.92 (1H, d, J=6.3 Hz), 2.63 (2H, m), 1.48 (2H, m), 1.14 (1H, m) and 1.05, 0.68 (17H, m). $^{13}$C-NMR; δ (CD$_3$OD), 175.3, 171.5, 163.4, 109.5, 73.1, 62.0, 49.0, 48.2, 48.0, 43.4, 39.6, 35.2, 27.1, 23.6 and 22.4. IR;ν$_{max}$(KBr); 3300, 3029, 2958, 2871, 2362, 1638, 1535, 1454, 1398, 1369, 1250, 1214, 1145, 1091, 1073, 1032, 1008 and 974 cm$^{-1}$.

EXAMPLE 10

2S-Allyl-N$^4$-(1-cyclopropylcarbamoyl-2,2-dimethyl-propyl)-N$^1$-hydroxy-3R-isobutyl-succinamide

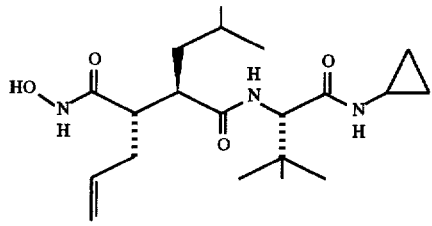

STEP A:
2R,S-Allyl-3R-isobutyl-succinic acid-4-tert-butyl ester (1:9, RS:RR)

To a stirred solution of 3R-isobutyl-succinic acid-4-tert-butyl ester (prepared according to the method described in WO 92/13831) (5 g, 21.7 mmol) in dry THF (100 ml), under an argon atmosphere, at −78° C., was added 1.5M LDA (31.8 ml, 47.7 mmol) dropwise via cannula. After stirring the solution at −78° C. for 1 hour, allyl bromide (2.44 ml, 28.2 mmol) was added dropwise via syringe. The resulting solution was allowed to warm to room temperature over a 2 hour period. Methanol (10 ml) was added and the solution stirred at room temperature. After 30 minutes the reaction mixture was concentrated under reduced pressure. The residue was taken up in dichloromethane (100 ml) and washed with 1M HCl (100 ml) and brine (100 ml). The dichloromethane layer was dried over MgSO$_4$, filtered and solvent removed under reduced pressure to give the title compound as a golden oil (5.6 g, 97%) (1:9, RS:RR) $^1$H-NMR; δ (CDCl$_3$ major diastereoisomer), 5.78-5.63 (1H, m), 5.01–5.11 (2H, m), 2.57–2.72 (2H, m), 2.37 (2H, m), 1.52–1.67 (2H, m), 1.42 (9H, s), 1.37 (1H, m) and 0.90 (6H, d, J=6.3 Hz). $^{13}$C-NMR; δ (CDCl$_3$ major diastereoisomer) 181.1, 172.9, 134.6, 117.3, 81.2, 47.8, 44.3, 38.4, 27.9, 25.9, 23.5, and 21.5.

STEP B:
2S-Allyl-3R-isobutyl-succinic acid-4-tert-butyl ester dicyclohexylamine salt (i) To a stirred solution of 2R,S-Allyl-3R-isobutyl-succinic acid-4-tert-butyl ester (1:9, RS:RR) (5.11 g, 18.9 mmol) in dry THF (100 ml) under argon at −78° C. was added 1.5M LDA (27.7 ml, 41.6 mmol) via cannula. The reaction mixture was warmed to room temperature over a 2 hour period then cooled back to −78° C. and methanol (8 ml) was added via syringe. The reaction was then allowed to warm to room temperature for a further 2 hours. The solvent was removed under reduced pressure. The residue was taken up in dichloromethane (150 ml) and washed with 1M HCl (150 ml) and brine (150 ml). The dichloromethane layer was dried over MgSO$_4$ and the solvent removed under reduced pressure to yield the title compound (3:2, RS:RR), as a brown oil (4.7 g, 92%).

(ii) Utilising the epimerisation procedure described above, but employing a reaction temperature of −78° C. after addition of LDA in lieu of allowing the reaction mixture to warm to room temperature yielded the title compound, as the major diastereomer as a brown oil (4.6 g, 98%) (3:1, RS:RR). $^1$H-NMR; δ (CDCl$_3$, major diastereoisomer), 11.60 (1H, br s), 5.75-5.61 (1H, br m), 5.06-4.96 (2H, br m), 2.70-2.52 (2H, br m), 2.36-

2.19 (2H, br m), 1.65-1.44 (2H, br m), 1.40 (9H, s), 1.13 (1H, m) and 0.86 (6H, dd, J=4.4, 2.1 Hz). $^{13}$C-NMR; δ (CDCl$_3$, major diastereoisomer) 180.7, 172.2, 134.6, 117.1, 81.0, 48.6, 45.7, 38.9, 34.8, 33.4, 27.9, 26.2 and 21.2.

(iii) The above reaction was repeated and the combined products (36.85 g, 136 mmol) were dissolved in hexane and the solution allowed to stand overnight before filtering through glass microfibre filter papers (Whatman GFF) to remove a small amount of a coloured solid. Dicyclohexylamine (27 ml, 136 mmol) was added to the filtrate: crystallisation commenced after approximately 30 minutes. The mixture was chilled in a refridgerator overnight and the product was collected by filtration, washed with cold hexane and dried under vacuum. Yield: 14.19 g (23%). $^1$H-NMR δ (CDCl$_3$),6.89-6.58 (2H, m), 5.76 (1H, m), 5.08-4.91 (2H, m), 2.99-282 (2H, m) 2.53-2.26 (4H, m), 2.09-1.93 (4H, m), 1.86-1.56 (8H, m), 1.54-0.99 (11H,m), 1.42 (9H, s), 0.92 (3H, d, J=6.5 Hz), 0.87 (3H, d, J=6.5 Hz). $^{13}$C-NMR; δ (CDCl$_3$ single diastereoisomer), 179.0, 173.9, 135.9, 115.7, 79.7, 52.1, 50.8, 49.7, 41.2, 35.9, 29.2, 29.1, 27.9, 26.5, 25.1, 24.6, 24.0 and 21.5.

STEP C:

N$^α$-Benzyloxycarbonyl-L-tert-leucine-N-cyclopropylamide

N$^α$Benzyloxycarbonyl-L-tert-leucine(5 g, 18.79 mmol) was dissolved in DMF (30 ml) and the solution was cooled to 0° C. and stirred during the addition of HOBt (3.04 g, 22.55 mmol) and EDC (4.32 g, 22.55 mmol). The mixture was allowed to warm to room temperature, stirred for a further 1 hour then cooled back to 0° C. Cyclopropylamine (2.35 ml, 27.63 mmol) was then added dropwise and the mixture was warmed to room temperature then stirred for 48 hours. Solvent was evaporated and the residue dissolved in ethyl acetate and washed successively with 1N HCl and 1N Na$_2$CO$_3$ before drying over anhydrous MgSO$_4$. The solution was filtered and the solvent was evaporated to a white solid (4.95 g, 87%). $^1$H-NMR; δ (CDCl$_3$), 7.32 (5H, m), 6.50 (1H, s), 5.72 (1H, d, J=9.1 Hz), 5.05 (2H, m), 3.90 (1H, d, J=9.4 Hz), 2.69 (1H, m), 0.98 (9H, s), 0.73 (2H, m) and 0.49 (2H, m).

STEP D:

L- tert- Leucine- N-cyclopropylamide

N$^α$- Benzyloxycarbonyl-L-tert-leucine-N-cyclopropylamide (4.59 g, 15.09 mmol) was dissolved in ethanol (90 ml) and cyclohexene (10 ml) and 10% palladium on charcoal (460 mg) were added. The mixture was heated at reflux for 1 hour after which time no starting material was detectable (TLC). The catalyst was removed by filtration and the solvent evaporated to leave the title compound as a colourless oil. Yield: 1.57 g (61%). 1H-NMR; δ (CDCl$_3$), 6.84 (1H, br s), 3.02 (1H, s), 2.68 (1H, m) 0.95 (9H, s), 0.74 (2H, m) and 0.47 (2H, m).

STEP E:

2-[1-(1-Cyclopropylcarbamoyl-2,2-dimethyl-propylcarbamoyl)-3-methyl-butyl]-pent-4-enoic acid-tert-butyl ester 2S-Allyl-3R-isobutyl-succinic acid-4-tert-butyl ester dicyclohexylamine salt (3.50 g, 7.72 mmol) and L-tert-leucine-N-cyclopropylamide (1.57 g, 9.27 mmol) were dissolved together in ethyl acetate (100 ml) and HOBt (1.04 g, 7.72 mmol) and EDC (1.48 g, 7.72 mmol) were then added. The mixture was heated under reflux for 2 hours then cooled to room temperature and precipitated material removed by filtration. The solution was washed three times with water, once with saturated Na$_2$CO$_3$ and once with 1N HCl, dried (MgSO$_4$), filtered and evaporated to dryness to provide the title compound as a white solid (2.05 g, 63%). 1H-NMR; δ (CDCl$_3$), 6.34 (1H, m) 5.76 (1H, m), 5.04 (2H, m), 4.21 (1H, d, J=9.2 Hz), 2.55 (2H, m), 223(1H, t,J=6.9 Hz, 7.5 Hz), 1.66 (1H, m), 1.45 (9H, s), 1.09 (11H, m), 0.88 (3H, d, J=6.4 Hz), 0.84 (3H, d, J=6.6 Hz), 0.78 (2H, m) and 0.49 (2H, m).

STEP F:

2-[1-(1-Cyclopropylcarbamoyl-2,2-dimethyl-propylcarbamoyl)-3-methyl-butyl]-pent-4-enoic acid 2-[1-(1-Cyclopropylcarbamoyl-2,2-dimethyl-propylcarbamoyl)-3-methyl-butyl]-pent-4-enoic acid-tert-butyl ester (2.05 g, 4.83 mmol) was dissolved in dichloromethane (7 ml) and TFA (7 ml). The mixture was allowed to stand at 0°-5° C. overnight then solvent was evaporated under reduced pressure, azeotroping with three times toluene to provide the title compound as a white solid which was recrystallised from ethyl acetate. Yield: 1.81 g (74%). 1H-NMR; δ (CD$_3$OD), 8.19 (1H, br s), 7.95 (1H, d, J=9.2 Hz), 5.72 (1H, m), 4.98 (2H, m), 4.19 (1H, d, J=9.3 Hz), 2.76 (1H,m), 2.56 (2H, m) 2.23 (1H, m), 1.59 (1H, m), 1.37 (1H, m), 0.96 (9H, s), 0.87 (3H, d,J=6.5 Hz), 0.81 (3H, d, J=6.6 Hz), 0.68 (2H, m) and 0.43 (2H, m).

STEP G:

2S-Allyl-N$^4$-(1 -cyclopropylcarbamoyl-2,2-dimethyl-propyl)-N$^1$-hydroxy-3R-isobutyl-succinamide 2-[1-(1-Cyclopropylcarbamoyl-2,2-dimethyl-propylcarbamoyl)-3-methyl-butyl]-pent-4-enoic acid (1.37 g, 3.74 mmol) was dissolved in DMF (20 ml) and the solution was cooled to 0° C. during the addition of HOBt (0.61 g, 4.49 mmol) and EDC (0.86 g, 4.49 mmol). The mixture was stirred at 0° C. for 1 hour then at room temperature for 2 hours to ensure complete formation of the active ester. The solution was cooled back to 0° C. and hydroxylamine hydrochloride (0.46 g, 6.73 mmol) was added, followed by NMM (0.74 ml,6.73 mmol) and the reaction mixture was allowed to warm to room temperature then stirred overnight. The solvent was removed in vacua and the residue was triturated with a mixture of diethyl ether (25 ml) and water (25 ml) and the mixture was left to stand for 2 hours. The resulting solid was collected by filtration, recrystallised several times from ethyl acetate—hexane and dried under high vacuum at 60° C. for 24 hours to afford the title compound (0.44 g, 31%; single diastereoisomer) m.p. 225°–226° C. $^1$H NMR; δ (CD$_3$OD), 8.17 (1H, d, J=3.2 Hz), 8.05 (1H, d, J=9.1 Hz), 5.60 (1H, m), 4.96 (2H, m), 4.19 (1H, d, J=9.2 Hz), 2.61 (2H, m), 2.16 (2H, m), 1.47 (1H, m), 1.33 (1H, m), 1.01 (1H, m), 0.97 (9H, s), 0.86 (3H, d, J=6.4Hz), 0.79 (3H, d, J=6.6 Hz), 0.67 (2H, m), and 0.41 (2H, m). $^{13}$C-NMR; d (CD$_3$OD), 176.5, 173.9, 172.4, 136.0, 117.5, 62.1, 41.8, 36.4, 35.1, 27.3, 27.1, 24.4, 23.2, 23.1, 22.0, 6;5 and 6.4. IR;v$_{max}$ (KBr); 3289, 2858, 1633, 1530, 1368, 1260 cm$^{-1}$. Found: C, 62.56%, H, 9.21% N, 10.96%; C$_{20}$H$_{35}$N$_3$O$_4$.0.1 H$_2$O requires C, 62.67%, H, 9.26% N, 10.96%.

The following additional compound was prepared by the methods of Example 10 using the appropriate starting materials:

EXAMPLE 11

2S-Allyl-N⁴-(1 S-cyclopropylcarbamoyl-2-mercapto-2-methyl-propyl)-N¹-hydroxy-3R-isobutyl-succinamide

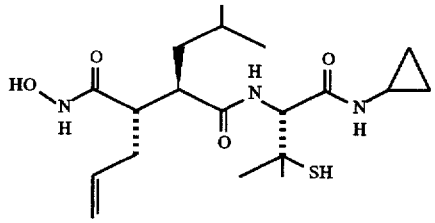

Off-white foam. m.p. 190.5°–192.5° C. $^1$H NMR; δ (CD$_3$OD), 5.57 (1H, m), 4.86 (2H, m), 4.33 (1H, s), 2.54 (2H, m), 2.20 (3H, br m), 1.49-1.25 (8H, 2s and br m), 107 (1H, m), 0.78 (3H, d, J=6.6 Hz), 0.73 (3H, d, J=6.6 Hz), 0.59 (2H, m) and 0.38 (2H, m). $^{13}$C-NMR; δ (CD$_3$OD), 176.5, 172.9, 172.7, 136.1, 117.5, 62.6, 48.1, 46.7, 41.8, 36.4, 30.7, 29.9, 27.1, 24.4, 23.3, 22.3, 6.6 and 6.4. IR;ν$_{max}$(KBr); 3293, 3078, 2958, 2871, 1641, 1527, 1463, 1386 and 1259 cm$^{-1}$. Found: C 56.13, H 8.12, N 10.16%; C$_{19}$H$_{33}$N$_3$O$_4$S. 0.4 H$_2$O requires C 56.10, H 8.38, N, 10.33%.

EXAMPLE 12

N⁴-(1 S-Cyclopropylcarbamoyl-2,2-dimethyl-propyl)-N¹-hydroxy-3R-isobutyl-2S-(thiophen-2-ylsulfanylmethyl)-succinamide

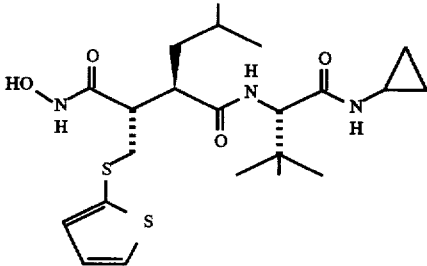

STEP A:
2-[1-(1-Cyclopropylcarbamoyl-2,2-dimethyl-propylcarbamoyl)-3-methyl-butyl]-malonic acid dibenzyl ester 2-Benzyloxycarbonyl-3R-isobutyl-succinic (prepared by the method described in EP 0 446 267) (10.79 g, 27.1 mmol) and L-tert-leucine-N-cyclopropylamide (5.54 g, 32.5 mmol) dissolved in ethyl acetate (200 ml) and treated with HOBt (4.39 g, 32.5 mmol) and EDC (6.23 g, 32.5 mmol). The reaction mixture was heated at reflux overnight then allowed to cool to room temperature. The solution was washed successively with 5% NaHCO$_3$ (2×200 ml), 5% citric acid (2×200ml) and brine, dried (anhydrous MgSO$_4$), filtered and evaporated to afford the title compound (15.21 g, 99%) as a yellow oil. $^1$H NMR; δ (CDCl$_3$), 7.89 (2H, m), 7.07 (10H, m), 4.88 (2H, m), 3.96 (1H, d, J=9.4 Hz), 3.53 (1H, d, J=10.1 Hz), 3.03 1H, m), 2.41 (1H,m), 1.23 (2H, m), 0.89 (1H, m), 0.72 (9H, s), 0.62 (3H, d, J=6.3 Hz), 0.56 (3H, d, J=6.3 Hz), 0.45 (2H, m) and 0.15 (2H, m).
STEP B:
2-[1-(1-Cyclopropyicarbamoyl-2,2-dimethyl-propylcarbamoyl)-3-methyl-butyl]-acrylic acid 2-[1-(1-Cyclopropylcarbamoyl-2,2-dimethyl-propylcarbamoyl)-3-methyl-butyl]-malonic acid dibenzyl ester (14.53 g, 25.7 mmol) was dissolved in ethanol (200 ml) and the solution was placed under a blanket of argon. 10% Palladium on charcoal (3.2 g) was added and a fine stream of hydrogen gas was passed through the suspension for 3h with stirring. TLC showed that all the starting material had been consumed. The system was purged with argon and the catalyst was removed by filtration. The filtrate was cooled and stirred in an ice bath and treated with piperidine (2.39 g, 28.1 mmol) which was added dropwise, followed by 37% formaldehyde solution (22.6 ml, ca. 257 mmol). The reaction mixture was allowed to warm slowly to room temperature, then stirred overnight. The solvents were removed under reduced pressure and the residual oil was partitioned between ethyl acetate (300 ml) and 1 M hydrochloric acid (300 ml). The organic layer was separated, washed with 1M HCl and brine, dried over MgSO$_4$, filtered and evaporated to dryness. The remaining pale brown foam (4.40 g, crude) contained a number of minor impurities but was used in Step C without purification. $^1$H-NMR; δ (CDCl$_3$), 8.34 (1H, d, J=10.0 Hz), 7.37 (1H, m), 6.47 (1H, s), 5.99 (1H, s), 4.50 (1H, d, J=9.9 Hz), 4.07 (1H, m), 2.73 (1H, m), 1.79 (1H, m), 1.52 (2H, m), 1.00-0.82 (1 5H, br m), 0.78 (2H, m) and 0.55 (2H, m).
STEP C:
3-(1-Cyclopropylcarbamoyl-2,2-dimethyl-propylcarbamoyl)-5-methyl-2-(thiophen-2-ylsulfanlmethyl)-hexanic acid 2-[1-(1-Cyclopropylcarbamoyl-2,2-dimethyl-propylcarbamoyl)-3-methyl-butyl]-acrylic acid (4.40 g, 12.4 mmol) was dissolved in methanol (10 ml) and placed under a blanket of argon prior to addition of 2-mercaptothiophene (4.5 ml). The mixture was stirred overnight at 60° C. under argon with the exclusion of light. The solvent was removed under reduced pressure to leave an oil to which was added cold diethyl ether (200 ml). The product precipitated on standing in an ice bath and was removed by filtration and washing with thoroughly with cold diethyl ether. The product was further purified by trituration with hot ethyl acetate and column chromatography (silica gel, gradient elution, 0–20% methanol in dichloromethane). Fractions were combined and evaporated to yield the title compound as an pale yellow solid (6.95 g, including minor impurities). $^1$H-NMR (CDCl$_3$, partial deuterium exchange); δ 8.10 (1H, m), 7.85 (1H, d, J=9.2 Hz), 7.35 (1H, m), 7.03 (1H, m), 6.88 (1H, m), 4.06 (1H, d, J=9.2 Hz), 2.85 (1H, m), 2.67 (2H, m), 2.51 (1H, m), 1.53 (1H, m), 1.25 (1H, m), 1.02 (1H, m), 0.87 (9H, s), 0.76 (3H, d, J=6.4 Hz), 0.71 (3 H, dJ=6.5 Hz), 0.61 (2H, m) and 0.32 (2H, m).
STEP D:
N⁴-(1 S-Cyclopropylcarbamoyl-2,2-dimethyl-propyl)-N¹-hydroxy-3R-isobutyl-2S-(thiophen-2-ylsulfanylmethyl)-succinamide The product from Step C (5.11 g) was converted to the title compound (2.39 g, 45%) by a method analogous to that described in Example 10 (Step G). White solid. m.p. 225.5°–226° C. $^1$H NMR; δ ((CD$_3$)$_2$SO), 10.52 (1H, s), 8.80 (1H, s), 7.77 (2H, m), 7.42 (1H, m), 6.94 (1H, m), 6.85 (1H, m), 3.95 (1H, d, J=9.8 Hz), 3.02 (1H, m), 2.54 (2H, m), 2.42 (1H, m), 2.24 (1H, m), 1.29 (1H, m), 1.10 (1H, m), 0.82 (1H, m), 0.71 (9H, s), 0.64 (3H, d, J=6.5 Hz), 0.59 (3H, d, J=6.4 Hz), 0.44 (2H, m) and 0.15 (2H, m). $^{13}$C-NMR; δ (CD$_3$OD) ,175.6, 173.8, 171.1, 134.9, 130.7, 128.6, 62.1, 41.6, 40.5, 35.1, 27.3, 27.0, 24.3, 23.0, 21.9, 6.5 and 6.4. IR; ν$_{max}$ (KBr); 3318, 3088, 2959, 2872, 1632, 1520, 1422, 1367, 1257, 1218, 1005, 849 and 706 cm$^{-1}$. Found: C 56.11, H 7.35, N 8.91%; C$_{22}$H$_{35}$N$_3$O$_4$S$_2$ requires C 56.26, H 7.51, N, 8.95%.

The following additional compound was prepared by the methods of Example 12 using 4-hydroxythiophenol in lieu of thiophene-2-thiol in Step C:

EXAMPLE 13

N⁴-(1 S-Cyclopropylcarbamoyl-2,2-dimethyl-propyl)-N¹-hydroxy-2S-(4-hydroxy-phenylsulfanylmethyl)-3R-isobutyl-succinamide

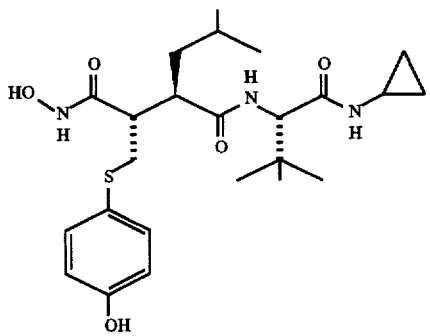

Pale yellow solid. $^1$H NMR; δ (CD$_3$OD), 7.06 (2H, m), 6.57 (2H, d, J=8.6 Hz), 4.08 (1H, s), 3.24 (1H, s), 3.03 (1H, m), 1.43 (1 H, m), 1.24 (1H, m), 0.87 (9H,s), 0.76 (3H, d, J=6.4 Hz), 0.70 (3H, d, J=6.5 Hz), 0.60 (2H, m) and 0.34 (2H, m). $^{13}$C-NMR; δ (CD$_3$OD), 175.9, 173.8, 170.8, 159.0, 134.5, 125.2, 117.3, 66.8, 62.0, 45.5, 41.6, 37.9, 35.2, 27.4, 24.3, 23.1, 22.0, 15.5 and 6.6. IR; v$_{max}$ (KBr); 3416, 2958, 2352, 1644, 1538, 1495,1368, 1266 and 833 cm$^{-1}$.

EXAMPLE 14

N⁴-(1 S-Cyclopropylcarbamoyl-2,2-dimethyl-propyl)-2S-(1,3-dioxo-1,3-dihydro-isoindol-2-ylmethyl)-N¹-hydroxy-3R-isobutyl-succinamide

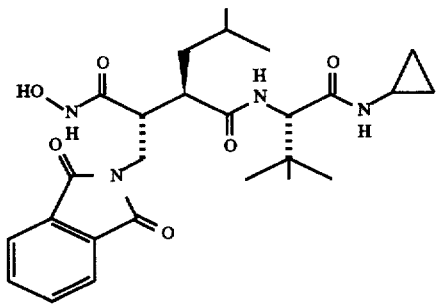

STEP A:
2-Benzyloxycarbonyl-2-(1,3-dioxo-1,3-dihydro-isoindol-2-ylmethyl)-3R-isobutyl succinic acid-4-benzyl ester-1-tert-butyl ester To an ice-cooled solution of 2-Benzyloxycarbonyl-3R-isobutyl succinic acid-4-benzyl ester-1 -tert-butyl ester (prepared by the method described in EP 0 446 267) (39.4 g, 86.78 mmol) in dry DMF (400 ml) was added sodium hydride (60% dispersion in mineral oil, 3.83 g, 95.46 mmol) with stirring. The reaction mixture was maintained at 0° C. for 20 mins then allowed to warm to room temperature and stirred for a further 2.5 h. After cooling to 0° C., N-(bromomethyl)phthalimide (25 g, 104.1 mmol) was added and the mixture was stirred for 0.5 h at 0° C. then at room temperature overnight. The solvent was removed under reduced pressure to leave an oil which was extracted with diethyl ether (400 ml) and the solid residues were removed by filtration. The filtrate was washed successively with water (300 ml), 1M HCl (300 ml) and brine (300 ml), dried over anhydrous MgSO$_4$ and filtered. The solution was concentrated in vacuo to leave a yellow oil which was purified by column chromatography (silica gel, 50% diethyl ether in hexane) to afford the title compound as a colourless oil (26.24 g, 49%). $^1$H-NMR; δ (CDCl$_3$), 7.78 (2H, m), 7.67 (2H, m), 5.28-5.05 (4H, br m), 4.54-4.35 (2H, br m), 3.03 (1H, m), 1.86 (1H, m), 1.68 (1H, m), 1.50 (9H, s), 1.49 (1H, m), 0.82 (3H, d, J=6.6 Hz) and 0.78 (3H, d, J=6.5 Hz).

STEP B:
2RS-(1,3-dioxo-1,3-dihydro-isoindol-2-ylmethyl)-3R-isobutyl succinic acid-1-tert-butyl ester 2-Benzyloxycarbonyl-2-(1,3-dioxo-1,3-dihydro-isoindol-2-ylmethyl)-3R-isobutyl succinic acid-4-benzyl ester-1-tert-butyl ester (26.24 g, 42.8 mmol) was deprotected by catalytic hydrogenolysis in ethanol, according to the method described in Example 10 (Step D). The solvent was removed under reduced pressure, the residue was dissolved in toluene (250 ml) and NMM (4.33 g, 42.8 mmol) was added. The mixture was heated under reflux for 2 h. Solvents were evaporated and the remaining oil was dissolved in ethyl acetate and the solution was washed with 5% citric acid (2×200 ml) and brine (200 ml), dried over anhydrous MgSO$_4$ and filtered. The solvent was removed, leaving the desired product as a yellow foam (16.58 g, including residual solvent) which was used directly in Step C. $^1$H-NMR; δ (CDCl$_3$), 7.83 (2H, m), 7.72 (10H, m), 4.12 (1H, m), 3.83 (1H, m), 3.21 (1H, m), 2.72 (1H, m), (1.81-1.55 (2H, br m), 1.48 (9H, s), 1.31 (1H, m) and 0.92 (6H, m).

STEP C:
2-(1,3-dioxo-1,3-dihydro-isoindol-2-ylmethyl)-3R-isobutyl succinic acid-4-benzyl ester-1-tert-butyl ester 2-(1,3-dioxo-1,3-dihydro-isoindol-2-ylmethyl)-3R-isobutyl succinic acid-1-tert-butyl ester (16.58 g, 42.56 mmol) was dissolved in dry DMF and placed under a blanket of argon. The solution was cooled in an ice bath, benzyl bromide (5.56 ml, 46.82 mmol) and anhydrous sodium carbonate (4.96 g, 46.82 mmol) were added and the mixture was left to stir overnight at room temperature. The solvent was removed under reduced pressure and the residual oil was dissolved in diethyl ether (300 ml) and washed successively with water (2×200 ml), 1M HCl (2×200 ml) and brine (200 ml). The organic phase was dried (anhydrous MgSO$_4$), filtered and evaporated to a crude yellow oil which was purified by column chromatography (silica gel, gradient elution, 30–50% diethyl ether in hexane). The desired product was isolated as a pale yellow oil (18.2 g, 89%; 3:2 mixture of diastereoisomers). $^1$H-NMR; δ (CDCl$_3$), 7.78 (2H, m), 7.67 (2H, m), 7.24 (5H, m), 5.05 (2H, m), 4.18-4.04 (1H, br m), 3.81 (1H, br m), 3.15 (1H, m), 2.73 (1H, m), 1.72-1.53 (2H, br m), 1.50 (5.4H, s), 1.41 (3.6H, s), 1.11 (1H, m) and 0.90 (6H, m).

STEP D:
2-(1,3-dioxo-1,3-dihydro-isoindol-2-ylmethyl)-3R-isobutyl succinic acid-4-benzyl ester 2-(1,3-dioxo-1,3-dihydro-isoindol-2-ylmethyl)-3R-isobutyl succinic acid-4-benzyl ester-1-tert-butyl ester was deprotected by acidolysis with TFA according to the procedure described in Example 10 (Step F). The product was isolated as a pale yellow oil (16.54 g, including residual solvent) and was used without further purification. $^1$H-NMR; δ (CDCl$_3$, 3:2 mixture of diastereoisomers), 8.28 (1H, br s), 7.78 (2H, m), 7.68 (2H, m), 7.25 (5H, m), 5.08 (2H, m), 4.15 (1H, m), 3.89 (1H, m) 3.25 (1H, m), 2.88 (1H, m), 1.82-1.52 (2H, br m), 1.25 (1H, m), and 0.89 (6H, m).

STEP E:
3-(1 -Cyclopropylcarbamoyl-2,2-dimethyl-propylcarbamoyl)-2-(1,3-dioxo-1,3-dihydro-isoindol-2-ylmethyl)-5-methyl-hexanoic acid-1-benzyl ester 2-(1,3-dioxo-1,3-dihydro-isoindol-2-ylmethyl)-3R-isobutyl succinic acid-4-benzyl ester (2.71 g, 6.46 mmol)

was dissolved in ethyl acetate (100 ml), HOBt (1.03 g, 7.04 mmol) and EDC (1.47 g, 7.68 mmol) were added and the reaction mixture was stirred for 3.5 h to ensure complete formation of the activated ester. L-tert-Leucine-N-cyclopropyllamide (1.20 g, 7.04 mmol) was added and the reaction mixture was heated at reflux overnight. The solution was cooled before washing successively with 5% aq. $NaHCO_3$, (2×200 ml) and water (2×200 ml). The organic phase was dried (anhydrous $MgSO_4$), filtered and evaporated under reduced pressure to give the desired product as an inseparable 3:2 mixture of diastereoisomers (3.46 g, 94%). $^1H$-NMR ($CD_3OD$); δ 9.76 (0.6H, s), 9.58 (0.4H, s), 8.45 (1H, m), 8.23 (1H, m), 7.85-7.60 (5H, m), 7.23 (4H, m), 7.08 (2H, m), 5.05 (2H, m), 4.77 (0.6H, d), 4.58 (0.4H, d), 4.02 (2H, m), 3.28 (1H, m), 2.77 (1H, m), 1.79 (1H, m), 1.55 (b 2H, m), 1.07 (9H, m) and 0.80 (6H, m).
STEP F:
3-(1-Cyclopropylcarbamoyl-2,2-dimethyl-propylcarbamoyl)-2-(1,3-dioxo-1,3-dihydro-isoindol-2-ylmethyl)-5-methyl-hexanoic acid 3-(1-Cyclopropylcarbamoyl-2,2-dimethyl-propylcarbamoyl)-2-(1,3-dioxo-1,3-dihydro-isoindol-2-ylmethyl)-5-methyl-hexanoic acid-1-benzyl ester (3.46 g, 6.02 mmol) was dissolved in ethyl acetate (90 ml) and cyclohexene (10 ml) and the solution was placed under a blanket of argon. 10% palladium on charcoal catalyst (0.75 g) was added and the mixture was heated at reflux for 4 hours. The mixture was cooled and the catalyst was removed by filtration and the filtrate was evaporated to leave a pale yellow foam. Column chromatography (silica gel, gradient elution, 30 to 60% ethyl acetate in hexane) afforded the desired product as a white solid (1.2 g, 41%). $^1H$-NMR ($CD_3OD$); δ 8.30 (1H, m), 8.08 (1H, m), 7.81 (5H, m), 7.11 (1H, m), 4.11 (0.75H, m), 3.92 (0.25H, m), 3.76 (1 H, m), 3.13-2.85 (2H, br m), 1.72 (1H, m), 1.53 (2H, m), 1.14 (6.7H, s), 1.08 (2.3H, s) and 0.86 (6H, m).
STEP G:
$N^4$-(1S-Cyclopropylcarbamoyl-2,2-dimethyl-propyl)-2S-(1,3-dioxo-1,3-dihydro-isoindol-2-ylmethyl)-$N^1$-hydroxy-3R-isobutyl-succinamide 3-(1-Cyclopropylcarbamoyl-2,2-dimethyl-propyl carbamoyl)-2-(1,3-dioxo-1,3-dihydro-isoindol-2-ylmethyl)-5-methyl-hexanoic acid (1.20 g, 2.40 mmol) was converted to the corresponding hydroxamic acid by the method described previously (Example 10, Step G). Purification by column chromatography gave the desired product as a white solid. m.p. 213°-214° C. (decomposed). $^1H$ NMR; δ ($CD_3OD$), 7.67 (4H, m), 4.19 (1H, s), 3.94 (1H, m), 3.44 (1H, m), 2.74 (2H, m)2.52 (1H, m), 1.35 (3H, m), 0.94 (9H, s), 0.80 (3H, d, J=6.4 Hz), 0.73 (3H, d, J=6.6 Hz), 0.62 (2H, m) and 0.37 (2H, m). $^{13}C$-NMR; δ ($CD_3OD$), 175.7, 174.2, 171.8, 169.1, 161.9, 135.3, 133.3, 124.2, 62.2, 41.5, 39.4, 35.1, 27.4, 27.0, 24.4, 23.1, 21.9, 9.5 and 9.4. IR;$v_{max}$(KBr), 3426, 2958, 1773, 1718, 1642, 1527, 1468, 1432, 1397, 1368 and 1102 $cm^{-1}$

BIOLOGICAL EXAMPLE

The following table compares the in vitro potencies of compounds of the present invention with those of similar compounds known in the art where $R_4$=Me (Comparators 1 to 3).

Comparator 1:$N^4$-(2,2-Dimethyl-1S-methylcarbamoyl-propyl)-$N^1$-hydroxy-3R-isobutyl-succinamide Comparator 2:$N^4$-(2,2-Dimethyl-1S-methylcarbamoyl-propyl)-2S, $N^1$-dihydroxy-3R-isobutyl-succinamide Comparator 3:$N^4$-(2,2-Dimethyl-1S-methylcarbamoyl-propyl)-2S, $N^1$-dihydroxy-3R-(3-phenyl-propyl-succinamide The potency of compounds of the invention as inhibitors of collagenase was determined by the procedure of Cawston and Barrett, (Anal, Biochem., 99, 340–345, 1979), hereby incorporated by reference, whereby a 1 mM solution of the compound being tested, or a dilution thereof, was incubated at 37° C. for 16 hours with collagen and collagenase (buffered with 25 mM Hepes, pH 7.5 containing 5mM $CaCl_2$, 0.05% Brij 35 and 0.02% $NaN_3$). The collagen was acetylated $^{14}C$ collagen prepared by the method of Cawston and Murphy, (Methods in Enzymology, 80, 711, 1981), hereby incorporated by reference. The samples were centrifuged to sediment undigested collagen, and an aliquot of the radioactive supernatant removed for assay on a scintillation counter as a measure of hydrolysis. The collagenase activity in the presence of 1 mM of the test compound, or a dilution thereof, was compared to activity in a control devoid of inhibitor and the result reported below as that of inhibitor concentration effecting 50% inhibition of the collagenase activity ($IC_{50}$).

The potency of compounds of the invention as inhibitors of stromelysin was determined by the procedure of Cawston et al, (Biochem. J., 195, 159–165, 1981), hereby incorporated by reference, whereby a 1 mM solution of the compound being tested, or a dilution thereof, was incubated at 37° for 16 hours with stromelysin and $^{14}C$ acetylate casein (buffered with 25 mM Hepes, pH 7.5 containing 5 mM $CaCl_2$, 0.05% Brij 35 and 0.02% $NaN_3$). The casein was acetylated $^{14}C$ casein prepared by the method of Cawston et al (ibid). The stromelysin activity in the presence of 1 mM of the test compound, or a dilution thereof, was compared to activity in a control devoid of inhibitor and the result reported below as that of inhibitor concentration effecting 50% inhibition of the stromelysin activity ($IC_{50}$).

| Test Compound | Collagenase $IC_{50}$ (nM) | Stromelysin $IC_5$ (nM) |
| --- | --- | --- |
| Example 1 | 5 | 20 |
| Example 2 | 2 | 15 |
| Example 3 | 3 | 60 |
| Example 4 | 20 | 30 |
| Example 5 | 10 | 30 |
| Example 9 | 10 | 30 |
| Compartor 1 | 10 | 700 |
| Comparator 2 | 5 | 200 |
| Example 8 | 30 | 20 |
| Comparator 3 | 20 | 90 |

We claim:
1. A compound of formula (I):

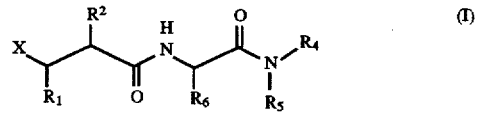

wherein
X is a —$CO_2H$ or —CONHOH group;
$R_1$ is hydrogen; ($C_1$–$C_6$)alkyl; ($C_2$–$C_6$)alkenyl; phenyl; substituted phenyl; phenyl ($C_1$–$C_6$)alkyl; substituted phenyl($C_1$–$C_6$)alkyl; heterocyclyl; substituted heterocyclyl; heterocyclyl($C_1$–$C_6$)alkyl; substituted heterocyclyl($C_1$–$C_6$)alkyl; a group BSO A— wherein n is 0, 1 or 2 and B is hydrogen or a ($C_1$–$C_6$) alkyl, phenyl, substituted phenyl, heterocyclyl, ($C_1$–$C_6$)acyl, phenacyl or substituted phenacyl group, and A represents ($C_1$–$C_6$)alkyl; amino; protected amino; acylamino; OH; SH; ($C_1$–$C_6$)alkoxy; ($C_1$–$C_6$)alkylamino; di-($C_1$–$C_6$)alkylamino; ($C_1$–$C_6$)alkylthio; aryl ($C_1$–$C_6$)

alkyl; amino $(C_1-C_6)$alkyl; hydroxy$(C_1-C_6)$alkyl, mercapto$(C_1-C_6)$alkyl or carboxy$(C_1-C_6)$alkyl wherein the amino-, hydroxy-, mercapto- or carboxyl- group are optionally protected or the carboxyl- group amidated; lower alkyl substituted by carbamoyl, mono (lower alkyl)carbamoyl, di(lower alkyl)carbamoyl, di(lower alkyl)amino, or carboxy-lower alkanoylamino;

$R_2$ is a $(C_1-C_6)$alkyl, $(C_2-C_6)$alkenyl, $(C_2-C_6)$alkynyl, phenyl$(C_1-C_6)$alkyl heteroaryl$(C_1-C_6)$alkyl, cycloalkyl$(C_1-C_6)$alkyl or cycloalkenyl$(C_1-C_6)$ alkyl group, any one of which may be optionally substituted by one or more substituents selected from the group consisting of $(C_1-C_6)$alkyl, —O$(C_1-C_6)$alkyl, —S$(C_1-C_6)$alkyl, —O-phenyl, —O$(C_1-C_6)$ alkylphenyl, halo and cyano (—CN);

$R_3$ is the characterising group of a natural or non-natural α amino acid in which any functional groups may be protected, PROVIDED that $R_3$ is not a fused or conjugated unsubstituted or substituted bicycloarylmethylene group;

$R_4$ is an optionally substituted $C_3-C_8$ cycloalkyl group or optionally substituted $C_4-C_8$ cycloalkenyl group;

$R_5$ is hydrogen or a $(C_1-C_6)$alkyl group; or a salt, hydrate or solvate thereof.

2. A compound as claimed in claim 1 wherein the stereochemistry is as follows:

C atom carrying the $R_1$ and X groups —S,

C atom carrying the $R_2$ group —R,

C atom carrying the $R_3$ group —S.

3. A compound as claimed in claim 1 or claim 2 wherein $R_1$ is hydrogen, methyl, ethyl, hydroxyl, allyl, thienylsulphanylmethyl, thienylsulphinylmethyl, thienylsulphonylmethyl or phthalimidomethyl.

4. A compound as claimed in claim 1 or claim 2 wherein $R_2$ iso-butyl, n-pentyl, n-hexyl, n-heptyl, n-octyl, n-nonyl, n-decyl, cyclohexylpropyl, phenylpropyl, 3-phenyl-prop-2-enyl, 4-chlorophenylpropyl, 4-methylphenylpropyl, 4-methoxyphenylpropyl, pyrid-4-ylpropyl, phenylbutyl, benzyloxybutyl, phenoxybutyl, propyloxymethyl and propylsulphanyl.

5. A compound as claimed in claim 1 or claim 2 wherein $R_3$ is benzyl, iso-butyl, 1-fluoro-1-methylethyl,1-hydroxy-1-methylethyl, 1-methoxy-1-methylethyl, S-benzyl-2-methyl-2-thiopropyl, 1-mercapto-1-methylethyl or t-butyl.

6. A compound as claimed in claim 1 or claim 2 wherein $R_4$ is cyclopropyl, 2-phenylcyclopropyl, cyclobutyl, cyclopentyl, cyclohexyl, cycloheptyl or cyclooctyl.

7. A compound as claimed in claim 1 or claim 2 in which $R_5$ is hydrogen, methyl or ethyl.

8. A compound selected from the group consisting of;

$N^4$-(1S-Cyclobutylcarbamoyl-2,2-dimethyl-propyl)-2S, $N^1$-dihydroxy-3R-isobutyl-succinamide $N^4$-(1S-Cyclopropylcarbamoyl-2,2-dimethyl-propyl)-2S, $N^1$-dihydroxy-3R-isobutyl-succinamide $N^4$-(1S-Cyclopentylcarbamoyl-2,2-dimethyl-propyl)-2S, $N^1$-dihydroxy-3R-isobutyl-succinamide $N^4$-(1S-Cyclohexylcarbamoyl-2,2-dimethyl-propyl)-2S, $N^1$-dihydroxy-3R-isobutyl-succinamide $N^4$-(1S-Cycloheptylcarbamoyl-2,2-dimethyl-propyl)-2S, $N^1$-dihydroxy-3R-isobutyl-succinamide $N^4$-(1S-Cyclopropylcarbamoyl-2-mercapto-2-methyl-propyl)-2S , N-dihydroxy-3R-isobutyl-succinamide $N^4$-(1S-Cyclopropylcarbamoyl-2,2-dimethyl-propyl)-2S, $N^1$-dihydroxy-3R-(3-phenyl-propenyl)-succinamide $N^4$-(1S-Cyclopropylcarbamoyl-2,2-dimethyl-propyl)-2S, $N^1$-dihydroxy-3R-(3-phenyl-propyl)-succinamide $N^4$-[2,2-Dimethyl-1S-(2-phenyl-cyclopropylcarbamoyl)-propyl]-2S, $N^1$-dihydroxy-3R-isobutyl-succinamide 2S-Allyl-$N^4$-(1-cyclopropylcarbamoyl-2,2-dimethyl-propyl)-$N^1$-hydroxy-3R-isobutyl-succinamide 2S-Allyl-$N^4$-(1S-cyclopropylcarbamoyl-2-mercapto-2-methyl-propyl)-$N^1$-hydroxy-3R-isobutyl-succinamide $N^4$-(1S-Cyclopropylcarbamoyl-2,2-dimethyl-propyl)-$N^1$-hydroxy-3R-isobutyl-2S-(thiophan-2-ylsulfanylmethyl)-succinamide $N^4$-(1S-Cyclopropylcarbamoyl-2,2-dimethyl-propyl)-$N^1$-hydroxy-2S-(4-hydroxy-phenylsulfanylmethyl)-3R-isobutyl-succinamide $N^4$-(1S-Cyclopropylcarbamoyl-2,2-dimethyl-propyl)-2S-(1,3-dioxo-1,3-dihydro-isoindol-2-ylmethyl)-$N^1$-hydroxy-3R-isobutyl-succinamide and salts, solvates or hydrates thereof.

9. A process for the preparation of a compound as claimed in claim 1 in which X is a hydroxamic acid group (—CONHOH), which process comprises:

(a) causing an acid of general formula (II)

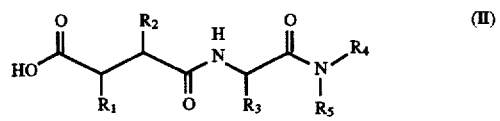

or an activated derivative thereof to react with hydroxylamine, O-protected hydroxylamine, or an N,O-diprotected hydroxylamine, or a salt thereof, $R_1$, $R_2$, $R_3$, $R_4$, and $R_5$ being as defined in general formula (I) except that any substituents in $R_1$, $R_2$, $R_3$, $R_4$, and $R_5$ which are potentially reactive with hydroxylamine, O-protected hydroxylamine, the N,O-diprotected hydroxylamine or their salts may themselves be protected from such reaction, then removing any protecting groups from the resultant hydroxamic acid moiety and from any protected substituents in $R_1$, $R_2$, $R_3$, $R_4$, and $R_5$; or (b) deprotecting a diprotected hydroxamic acid derivative of formula (IIb)

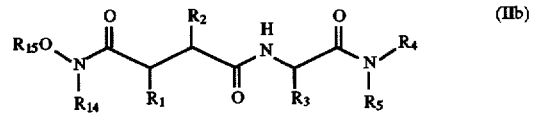

in which $R_1$, $R_2$, $R_3$, $R_4$, and $R_5$ are as defined in general formula (I), $R_{14}$ is an amino protecting group and $R_{15}$ is a hydroxyl protecting group.

10. A process for the preparation of a compound as claimed in claim 1 in which X is a carboxylic acid group (—COOH) which process comprises coupling an acid of formula (III) or an activated derivative thereof with an amine of formula (IV)

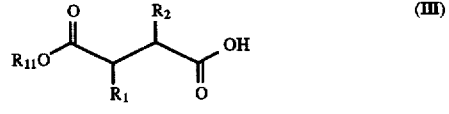

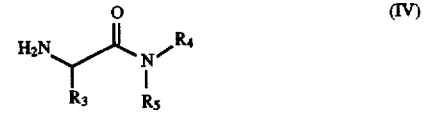

wherein $R_1$, $R_2$, $R_3$, $R_4$, and $R_5$ are as defined in general formula (I) except that any substituents in $R_1$, $R_2$, $R_3$, $R_4$, and $R_5$ which are potentially reactive in the coupling reaction may themselves be protected from such reaction, and $R_{11}$, represents a hydroxy protecting group, and subsequently removing the protecting group $R_{11}$, and any protecting groups from $R_1$, $R_2$, $R_3$, $R_4$, and $R_5$.

11. A pharmaceutical or veterinary composition comprising a compound as claimed in claim 1 or claim 2 together with a pharmaceutically or veterinarily acceptable excipient or carrier.

12. A pharmaceutical or veterinary composition as claimed in claim 11 which is adapted for oral administration.

* * * * *